United States Patent
Vitins et al.

(10) Patent No.: US 9,814,743 B2
(45) Date of Patent: Nov. 14, 2017

(54) POLYETHYLENE GLYCOL COMPOSITIONS FOR CONTROLLING RELAPSE OF HERPES LABIALIS, HERPES GENITALIS, AND HERPES ZOSTER

(75) Inventors: Peter Vitins, Oberohdorf (CH); Marcel Langenauer, Laupersdorf (CH); Paul Martin Scherer, Walchwil (CH)

(73) Assignee: DEVIREX AG, Walchwil (CH)

( * ) Notice: Subject to any disclaimer, the term of this patent is extended or adjusted under 35 U.S.C. 154(b) by 15 days.

(21) Appl. No.: 13/704,061

(22) PCT Filed: Jul. 8, 2011

(86) PCT No.: PCT/IB2011/001919
§ 371 (c)(1),
(2), (4) Date: Dec. 13, 2012

(87) PCT Pub. No.: WO2012/004669
PCT Pub. Date: Jan. 12, 2012

(65) Prior Publication Data
US 2013/0090389 A1     Apr. 11, 2013

Related U.S. Application Data

(60) Provisional application No. 61/362,329, filed on Jul. 8, 2010.

(51) Int. Cl.
*A61K 31/765* (2006.01)
*A61K 31/77* (2006.01)

(52) U.S. Cl.
CPC ............ *A61K 31/765* (2013.01); *A61K 31/77* (2013.01)

(58) Field of Classification Search
USPC ........................................................ 514/723
See application file for complete search history.

(56) References Cited

U.S. PATENT DOCUMENTS

| | | | |
|---|---|---|---|
| 4,762,715 A * | 8/1988 | Lukas et al. | 424/642 |
| 5,232,700 A | 8/1993 | Centifanto | |
| 6,387,398 B1 * | 5/2002 | Vollhardt et al. | 424/450 |

FOREIGN PATENT DOCUMENTS

| | | |
|---|---|---|
| DE | 20 2005 007363 | 8/2005 |
| DE | 202005007363 U1 | 8/2005 |
| EP | 0087161 A2 | 8/1983 |
| WO | WO 96/24367 A1 | 8/1996 |

(Continued)

OTHER PUBLICATIONS

Subrahmanyam, Addition of Antioxidants and PEG 4000 enhances the healing property of honey in burns, Annals of Burns and Fire Disasters Vol IX n.2.*

(Continued)

*Primary Examiner* — Kendra D Carter
*Assistant Examiner* — Taina D Matos Negron
(74) *Attorney, Agent, or Firm* — James S. Keddie; Bozicevic, Field & Francis LLP

(57) ABSTRACT

The present invention pertains generally to the field of therapy, and more specifically to the field of therapy for herpes simplex and herpes zoster, and more particularly, to methods of reducing the rate of relapse, delaying relapse, and/or preventing relapse of herpes labialis (cold sores on the lips), herpes genitalis (genital herpes), and herpes zoster (shingles, zona), by topical administration of polyethylene glycol (PEG), or a composition comprising PEG.

38 Claims, 1 Drawing Sheet

(56) References Cited

FOREIGN PATENT DOCUMENTS

| WO | WO0044347 A1 * | 1/2000 |
| WO | WO 2008/087034 A2 | 7/2008 |
| WO | WO 2012/004669 | 1/2012 |
| WO | WO 2012/004669 A1 | 1/2012 |
| WO | WO 2013/102885 A1 | 7/2013 |

OTHER PUBLICATIONS

Hull et al.,Valacyclovir and topical clobetasol gel for episodic treatment of herpes labialis: a patient-initiated, double-blind, placebo-controlled, pilot trial, JEADV 2009, 23, 263-267.*
Opstelten et al. Treatment and prevention of herpes labialis. Can Fam Physician (2008), vol. 54, pp. 1683-1687.*
Buenzli et al., Mar. 17, 2004, "Seroepidemiology of herpes simplex virus type 1 and 2 in western and southern Switzerland in adults aged 25-74 in 1992-93: a population-based study", BMC Infectious Diseases, vol. 4, No. 10.
Corey et al., Jun. 1982, "A trial of topical acyclovir in genital herpes simplex virus infections", New England J. Med., vol. 306, No. 22, pp. 1313-1319.
IPRP on PCT/IL32011/001919 dated Aug. 9, 2012.
ISR and WOISA for PCT/IB2011/001919 dated Oct. 18, 2011.
James et al., 2006, Andrews' Diseases of the Skin: Clinical Dermatology (Saunders Elsevier, ISBN 0-7216-2921-0), pp. 474-475.
Macrogols monograph, European Phamacopoeia 5.0 01/2005:1444, pp. 1950-1951.
MerckManual entry for Herpes Labialis (2009)—downloaded from http://unboundmedicine.com/merckmanual/ub on Feb. 5, 2012.
Opstelten et al., 2008, "Treatment and Prevention of Herpes Labialis", Can. Farn. Phys., vol. 54, pp. 1683-1687.
PEG monograph, downloaded from http://www.uspnf.com/uspnf/pub/data/v32272/usp32nf27s2__m66430.xml on Sep. 6, 2010.
Whitley et al., 1990, "Herpes simplex viruses", in Virology, (Fields, B.N., et al., eds., Raven Press, New York, USA), pp. 1852-1854.
Young et al., 1988, "Cross-sectional study of recurrent herpes labialis", Am. J. Epidemiol., vol. 127, pp. 612-625.
Fahim et al. Fertility and Sterility, Elsevier Science 28(3):394 (Mar. 1977) "New Treatment for Herpes Simplex Virus Type II (Ultrasound and Zinc, Urea, and Tannic Acid Ointment)".
Fahim et al. Archives of Andrology, Elsevier Science 4(1)79-85 (1980) "Treatment of Genital Herpes Simplex Virus in Male Patients".
Fahim et al. Journal of Medicine 11(2-3):143-167 ( 1980) "New Treatment for Herpes Simplex Virus Type 2 (Ultrasound and Zinc, urea and Tannic Acid Ointment") Part II: Female Patients.
Taylor et al. British Journal of Venereal Diseases 51(2) :125-129 (1975) "Comparison of the Treatment of Herpes Genitalis in Men with Proflavine Photoinactivation, Idoxuridine Ointment, and Normal Saline".
Fahim et al., 1977, New treatment for herpes simplex virus type II (ultrasound and zinc, urea, and tannic acid ointment), Fertility and Sterility, vol. 28, No. 3, p. 39.
Taylor et al., 1975 "Comparison of the treatment of herpes genitalis in men with proflavine photoinactivation, idoxuridine ointment, and normal saline", Brit. J. Venereal Diseases, vol. 51, No. 2, pp. 125-129.
Fahim et al., 1980, "Treatment of genital herpes simplex virus in male patients", Archives of Andrology, vol. 4, pp. 79-85.
Fahim et al., 1980, "New treatment for herpes simplex virus type 2 [ultrasound and zinc, urea and tannic acid ointment], Part II: Female Patients", Journal of Medicine, 1980, vol. 11, Nos. 2 & 3, pp. 143-167.
ISR and WOISA for PCT/IB2013/050097 dated Apr. 3, 2013.
IPRP for PCT/IB2013/050097 dated Jul. 17, 2014.

Aoki, Jan. 2003, "Contemporary antiviral drug regimens for the prevention and treatment of orolabial and anogenital herpes simplex virus infection in the normal host: four approved indications and 13 off-label uses", Canadian Journal of Infectious Diseases, vol. 14, No. 1, pp. 17-27.
Chon et al., Jul. 2007, "What are the best treatments for herpes labialis?", The Journal of Family Practice, vol. 56, No. 7, pp. 576-578.
Corey et al., Jun. 1982, "A trial of topical acyclovir in genital herpes simplex virus infections", New England Journal of Medicine, vol. 306, No. 22, pp. 1313-1319.
Corey et al., 1982, "Double-blind controlled trial of topical acyclovir in genital herpes simplex virus infections", The American Journal of Medicine, Acyclovir Symposium, pp. 326-334.
Corey et al., 1983, "Treatment of primary first-episode genital herpes simplex virus infections with acyclovir: results of topical, intravenous and oral therapy", Journal of Antimicrobial Chemotherapy, vol. 12, Suppl. B, pp. 79-88.
Cunningham et al., 2011, "Current management and recommendations for access to antiviral therapy for herpes labialis", Journal of Clinical Virology, doi: 10.1016/j.jcv.2011.08.003.
Fawcett et al., Sep. 1983, "Prophylactic topical acyclovir for frequent recurrent herpes simplex infection with and without erythema mulitforme", British Medical Journal, vol. 287, pp. 798-799.
Fiddian et al., 1983, "Successful treatment of herpes labialis with topical acyclovir", British Medical Journal, vol. 286, pp. 1699-1701.
Fiddian et al., 1983, "Topical acyclovir in the treatment of genital herpes: a comparison with systemic therapy", Journal of Antimicrobial Chemotherapy, vol. 12, Suppl. B, pp. 67-77.
Fiddian et al., 1983, "Treatment of herpes labialis", Journal of Infection, vol. 6, Supplement I, pp. 41-47.
Fiddian et al., 1983", Topical acyclovir in the management of recurrent herpes labialis", British Journal of Dermatology, vol. 109, pp. 321-332.
Gibson et al., 1986, "Prophylaxis against herpes labialis with acyclovir cream—a placebo-controlled study", Dermatologica, vol. 172, pp. 104-107.
Kennedy et al., Nov. 1981, "Treatment of erythema multiforme secondary to herpes simplex by prophylactic topical acyclovir", British Journal of Medicine, vol. 283, pp. 1360-1361.
Kinghorn et al., 1983, "Efficacy of topical acyclovir cream in first and recurrent episodes of genital herpes", Antiviral Research, vol. 3, pp. 291-301.
Luby et al., Jul. 1984, "A collaborative study of patient-initiated treatment of recurrent genital herpes with topical acyclovir or placebo", Journal of Infectious Diseases, vol. 150, No. 1, pp. 1-6.
Paterson et al., 2005, "Recurrent herpes labialis: assessment and non-prescription treatment", lesson material from MediResources, Inc.; pp. 1-21.
Shaw et al., Jul. 1985, "Failure of acyclovir cream in treatment of recurrent herpes labialis", British Medical Journal, vol. 291, pp. 7-9.
Spruance et al., Jul. 1982, "Treatment of herpes simplex labialis with topical acyclovir in polyethylene glycol", Journal of Infectious Diseases, vol. 146, No. 1, pp. 85-90.
Van Vloten et al., 1983, "Topical acyclovir therapy in patients with recurrent orofacial herpes simplex infections", Journal of Antimicrobial Chemotherapy, vol. 12, Suppl. B, pp. 89-93.
Worrall, Feb. 2009, "Herpes labialis", Clinical Evidence, 2009;09:1704, pp. 1-13.
Yeo et al., 1983, "Acyclovir in the management of herpes labialis", Journal of Antimicrobial Chemotherapy, vol. 12, Suppl. B, pp. 95-103.
"New therapeutic agent for herpes labialis 'Herpecia ointment' will be released: a switch OTC drug containing antiviral ingredient", press release from Taisho Pharmaceutical Co., Ltd. dated Sep. 25, 2007 (in Japanese with English translation).

* cited by examiner

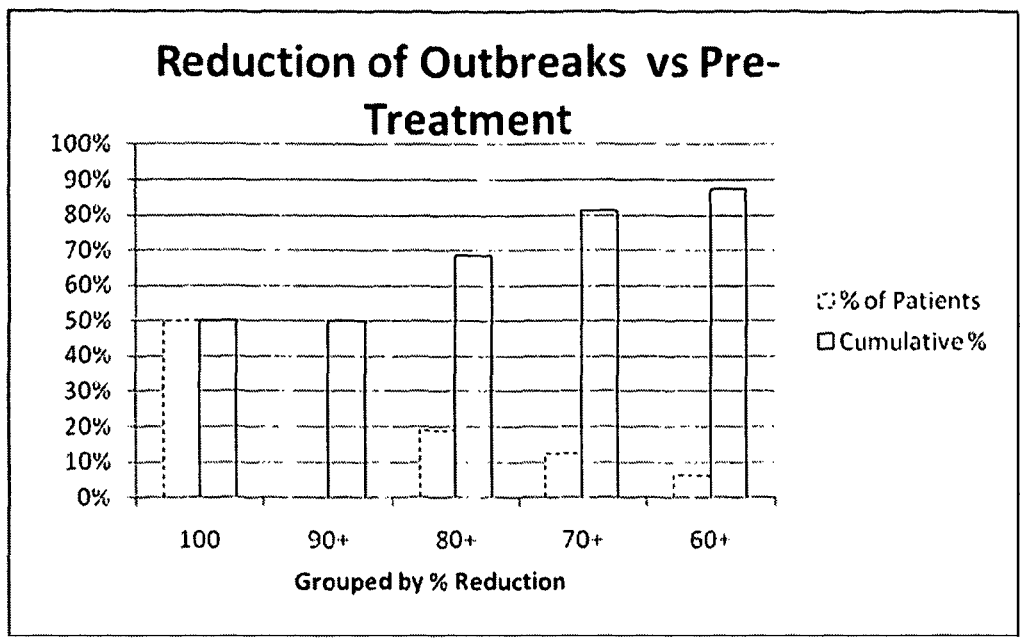

POLYETHYLENE GLYCOL COMPOSITIONS FOR CONTROLLING RELAPSE OF HERPES LABIALIS, HERPES GENITALIS, AND HERPES ZOSTER

RELATED APPLICATION

This application is a 35 U.S.C. §371 national phase application of PCT/IB2011/001919, filed Jul. 8, 2011 (WO 2012/004669). PCT/IB2011/001919 claims priority to U.S. patent application No. 61/362,329 filed Jul. 8, 2010, the contents of which are incorporated herein by reference in their entirety.

TECHNICAL FIELD

The present invention pertains generally to the field of therapy, and more specifically to the field of therapy for herpes simplex and herpes zoster, and more particularly, to methods of reducing the rate of relapse, delaying relapse, and/or preventing relapse of herpes labialis (cold sores on the lips), herpes genitalis (genital herpes), and herpes zoster (shingles, zona), by topical administration of polyethylene glycol (PEG), or a composition comprising PEG.

BACKGROUND

A number of publications are cited herein in order to more fully describe and disclose the invention and the state of the art to which the invention pertains. Each of these publications is incorporated herein by reference in its entirety into the present disclosure, to the same extent as if each individual publication was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Herpesviridae

The herpesviridae are a large family of DNA viruses, also known as herpesviruses. There are a number of distinct viruses in this family that are known to cause disease in humans, including: herpes simplex virus 1(HSV-1); herpes simplex virus 2 (HSV-2); varicella zoster virus (VZV); Epstein-Barr virus (EVB); cytomegalovirus (CMV); roseolovirus; and Kaposi's sarcoma-associated herpesvirus (KSHV).

Both the herpes simplex viruses (HSV-1 and HSV-2) and the varicella zoster virus (VZV) belong to the same viral subfamily (alphaherpesvirinae).

Herpes Simplex Virus (HSV)

Herpes simplex viruses have a diameter of 140 to 180 nm, and therefore are classed among the large viruses. They possess an ikosaedric capsid which contains a linear, double stranded DNA. The capsid is surrounded by a virus envelope; this fact causes the sensitiveness of the virus to soaps, detergents and mild disinfectants.

About 80% of the worldwide population is positive for HSV antibodies (see, e.g., Whitley, 1990) and consequently the herpes simplex virus is distributed all over the world. In the United States, the lifetime prevalence of recurrent herpes labialis is estimated at 20% to 40%, with approximately 100 million episodes occurring in the country every year (see, e.g., Young et al., 1988). In Switzerland, about 70% of the adult population is positive for HSV-1 antibodies and about 20% is positive for HSV-2 antibodies (see, e.g., Buenzli et al., 2004).

HSV-1 is transmitted via saliva contact, or smear infection, whereas HSV-2 is transmitted via close mucosa contact. HSV-1 is normally acquired during infancy, via the oral mucosa where it causes gingivostomatitis (a very painful inflammation in the mouth). Afterwards the viruses migrate along the axons to the CNS (central nervous system), where they stay latent in the ganglion trigeminale (Gasseri). After reactivation (endogenous recrudescence), which can be caused by psychic stress, isolation, fever, traumas, menstruation, other infections or immunosuppressive therapy, they migrate to the periphery in the same way, where they cause cold sores (Herpes labialis). There is a very high density of nerve endings in the lips; those epithelial layers are important for the reproduction of the virus.

Despite a present immunity, these recrudescences are always possible, because the virus migrates along the nerve pathway and does not migrate into the intercellular space. This means that the immune system has no possibility to attack the viruses. Some complications are therefore possible; one of them is herpetic keratoconjunctivitis or the highly lethal Herpes encephalitis (which has an untreated lethality of up to 80%).

Initial infection with HSV-2 normally takes place during sexual intercourse and concerns the urogenital tract. This infection can happen even though the host tests positive for HSV-1. The HSV-2 virus stays latent in the lumbosacral ganglions or in the peripheral tissue from where it causes the so called Herpes genitalis symptoms. Neurological complications are rare and more benign than with HSV-1 infection. However, there is one complication with high mortality: the infection of the neonate (Herpes neonatorum).

Herpes Labialis

Herpes labialis is a disease which is triggered by the herpes simplex virus (HSV). There are two types of Herpes simplex viruses which are called HSV-1 and HSV-2, both of which belong to the genus of the Simplex viruses of the family Herpes viridae.

The incubation time of Herpes labialis is typically from 2 to 12 days. The initial signs and symptoms of reactivation of Herpes labialis include: a feeling of tension; hypersensitivity of the skin; tingling, burning, and/or itching followed by a delayed reepithelialisation; crusting (which is often pus-filled) and erosions. In some rare cases, the lymph nodes can be swollen.

In addition to the neurologic and internistic diagnostic procedure, there is also a possibility to detect the virus in the blood, with antibody testing. However, confirmation of the specific virus is only performed in severe cases. Even in generalized and disseminated HSV-infections, the detection of HSV-IgG and HSV-IgM antibodies can not be done or can only be done very late.

The lytic cycle of HSV in epithelial cells includes entry, uncoating, viral transcription, DNA replication in the nucleus, particle assembly and exit from the cell. As a result of this process, a primary infection is triggered. Some of the viruses enter sensory neuron terminals and travel retrogradely to the nucleus, where they establish latency. Epithelial cells are re-infected following anterograde transport of viral particles shedding from the neuron. This re-infection leads to asymptomatic shedding or recurrent lesions.

Current Treatments for Herpes Labialis

For the abatement of Herpes labialis, a number of antivirals are available. The "gold standard", however, is acyclovir, a nucleoside analog of the guanine base. Because of its low bioavailability, some other antivirals have been developed (e.g., pencyclovir and its derivatives famciclovir and valaciclovir etc.). The acyclovir molecule is transformed (only in infected cells) to acyclovir-monophosphate by the viral thymidine kinase. This kinase is much more effective on phosphorylation, than the cellular thymidine kinase. Afterwards, the monophosphate form of acyclovir is converted into the triphosphate form (acyclovir-triphoshate) by cellular thymidine kinase.

For slight or rare outbreaks of Herpes labialis, the application of 5% acyclovir cream is sufficient. This cream is applied directly onto the cold sore 5 times daily, typically for 5 days, and a treatment period of 10 days should not be exceeded.

The current treatment for episodic recurrent Herpes labialis is as follows:

TABLE 1

| | |
|---|---|
| Acyclovir (Zovirax ®) | 5 × 200 mg p.o. per day for 5 days |
| Valaciclovir (Valterx ®) | 2 × 500 mg p.o. per day for 5 days |
| Famciclovir (Famvir ®) | 2 × 125 mg p.o. per day for 5 days |

The current treatment for virostatic suppression therapy for frequent relapses of recurrent Herpes labialis is as follows:

TABLE 2

| | |
|---|---|
| Acyclovir (Zovirax ®) | 2 × 400 mg p.o. per day for at least 6-12 months |
| Valaciclovir (Valterx ®) | 1 × 500 mg p.o. per day for at least 6-12 months; or 2 × 500 mg p.o per day for at least 6-12 months |
| Famciclovir (Famvir ®) | 2 × 250 mg p.o. per day for at least 6-12 months |

The above treatments are very expensive, especially when long-term treatment is required. This often also causes a reduction in patient compliance with the treatment regimen. Additionally, in recent years, there is an increase in the amount of viruses resistant to acyclovir, which can also reduce treatment efficacy.

Consequently, there is an important need for alternative treatments for HSV infections and for diseases and disorders associated with, triggered by, or caused by, infection by herpes simplex virus (HSV), including, for example, herpes labialis.

The inventors have discovered that, surprisingly and unexpectedly, polyethylene glycol (PEG) applied topically onto the lips and surrounding facial skin of a patient reduces the rate of relapse, delays relapse, and/or prevents relapse of herpes labialis.

Many treatments for herpes labialis have been described. Usually, the treatment involves the use of a formulation comprising one or more therapeutic agents (e.g., one or more agents for the treatment of herpes labialis and/or the underlying viral infection). In some cases, the formulation additionally includes polyethylene glycol (PEG).

However, in each case, the PEG is included for its formulation properties, and not because of any recognition of its therapeutic value. Nowhere has it been suggested that polyethylene glycol itself is useful or effective in therapy for viral infections, let alone for reducing the rate of relapse, delaying relapse, and/or preventing relapse of herpes labialis, herpes genitalis, or herpes zoster.

Also, in each case, the formulation is intended for treatment of acute herpes labialis (e.g., treatment of the symptoms of herpes labialis; to reduce the severity of the symptoms; to reduce the duration of the relapse; to promote healing, etc.). In each case, the formulation is administered at the beginning of relapse (i.e., in the prodromal phase) or during the relapse (i.e., in the acute phase). Nowhere has it been suggested that such formulations should be administered as a prophylactic, even when no symptoms appear, in order to reduce the rate of relapse, delay relapse, and/or prevent relapse.

For example, international patent publication number WO 2008/087034 A2 describes cyclodextrin formulations and their use in the treatment of viral infections, including treatment of cold sores. See, e.g., page 3, lines 23-24 therein. The formulations may contain, for example, polyethylene glycol, as an optional additional component. See, e.g., pages 15-16 therein. Nowhere in this document is there any teaching or suggestion that polyethylene glycol itself is useful or effective in therapy for viral infections, such as herpes labialis. Nowhere in this document is there any teaching or suggestion that polyethylene glycol itself is useful or effective for reducing the rate of relapse, delaying relapse, and/or preventing relapse of herpes labialis, herpes genitalis, or herpes zoster.

Similarly, U.S. Pat. No. 4,762,715 describes lipstick formulations comprising certain antiherpetic agents (heparin and zinc sulphate) for treatment of herpes labialis. Example 1 therein describes the preparation of a lipstick using a mixture of: PEG 1000; PEG 4000; PEG 400; polyoxyethylene sorbitan monostearate; polyoxyethylene sorbitan monooleate; heparin sodium; and zinc sulphate heptahydrate. Nowhere in this document is there any teaching or suggestion that polyethylene glycol itself is useful or effective in therapy for viral infections such as herpes labialis. Nowhere in this document is there any teaching or suggestion that polyethylene glycol itself is useful or effective for reducing the rate of relapse, delaying relapse, and/or preventing relapse of herpes labialis, herpes genitalis, or herpes zoster. Instead, polyethylene glycol was chosen as a preferred carrier, as is often the case in pharmaceutical formulation.

BRIEF DESCRIPTION OF THE DRAWINGS

FIG. 1 is a bar graph illustrating the reduction in the number of outbreaks (relapses) of herpes labialis in the patients of the study described herein. Both % of patients and cumulative % of patients are reported for each of 100%, 90+%, 80%+, 70%+, and 60%+ reduction in the number of outbreaks (relapses).

SUMMARY OF THE INVENTION

One aspect of the invention pertains to a method of reducing the rate of relapse, delaying relapse, and/or preventing relapse of herpes labialis, herpes genitalis, or herpes zoster in a patient, comprising topically administering to said patient a therapeutically effective amount of: polyethylene glycol or a composition comprising polyethylene glycol (PEG), as described herein.

Another aspect of the invention pertains to polyethylene glycol (PEG), as described herein, for use in therapy.

Another aspect of the invention pertains to polyethylene glycol (PEG), as described herein, for use in a method of reducing the rate of relapse, delaying relapse, and/or preventing relapse of herpes labialis, herpes genitalis, or herpes zoster by topical administration.

Another aspect of the invention pertains to use of polyethylene glycol (PEG), as described herein, in the manufacture of a medicament for reducing the rate of relapse, delaying relapse, and/or preventing relapse of herpes labialis, herpes genitalis, or herpes zoster by topical administration.

Another aspect of the invention pertains to a formulation suitable for topical administration comprising PEG, as described herein.

As will be appreciated by one of skill in the art, features and preferred embodiments of one aspect of the invention will also pertain to other aspects of the invention.

DETAILED DESCRIPTION OF THE INVENTION

The inventors have discovered that, surprisingly and unexpectedly, polyethylene glycol (PEG) applied topically onto the lips of a patient is effective in reducing the rate of relapse, delaying relapse, and/or preventing relapse of herpes labialis.

As demonstrated by the clinical study described herein, twice daily topical administration of PEG onto the lips of patients who were suffering at least 8 relapses of herpes labialis per year caused a substantial reduction in the rate of relapse. In many cases, the prophylactic therapy appears to have delayed relapse indefinitely.

Without wishing to be bound to any particular theory, it is postulated that the hygroscopic properties of the PEG may contribute to its effectiveness. It is postulated that regular (prophylactic) therapy with PEG changes the skin environment, and that the resulting skin conditions are less suitable for virus replication, proliferation, and/or activity. In general terms, hygroscopic PEG binds water; if it is applied on the lips, skin, or a wet surface, the PEG binds the water from the corresponding matrix. Also, it is likely that not only water will be bound, but also other components, possibly glycerol, proteins, etc. that are dissolved in water (giving rise to a "washing-out" effect). It is postulated that when PEG is applied regularly, it is has a positive influence on the composition of the skin that is effective in reducing the rate of relapse, delaying relapse, and/or preventing relapse of, for example, herpes labialis.

In addition to being particularly effective, PEG has other important advantages. PEG is used in a wide variety of applications, ranging from industrial manufacturing to medicine, and sophisiticated methods for its manufacture, purification, and handling are already known. PEG is considered to be extremely safe for humans and appears on the list of Substances Generally Recognized as Safe (GRAS). Topical adminstration of PEG may be expected to have few, if any, undesired side-effects. In sharp contrast, all of the established antiviral agents (acyclovir, valaciclovir, famciclovir, foscamet, or penciclovir) are systemic, and suffer from a range of undesired side-effects (e.g., nausea, vomiting, diarrhea, loss of appetite, stomach pain, headache, feeling light-headed, swelling in hands or feet, etc.). In addition, it may expected that the cost of suitable PEG formulations would be less than the cost of comparable formulations of established systemic antiviral agents. Overall, PEG may be expected to enjoy high patient compliance (almost certainly higher than patient compliance for the established systemic antiviral agents).

For the avoidance of doubt, it is not asserted that the methods described herein prevent viral infection (e.g., prevent infection with HSV-1, HSV-2, or VZV). Instead, the methods described herein are useful in therapy for diseases and disorders associated with, triggered by, or caused by, viral infection (i.e., diseases and disorders associated with, triggered by, or caused by, HSV-1, HSV-2, or VZV infection). In this way, the methods described herein may be described as palliative care, in the sense of preventing and/or relieving the symptoms of viral infection (e.g., HSV-1, HSV-2, or VZV infection).

Polyethylene Glycol (PEG)

Polyethylene glycol (PEG), also known as polyethylene oxide (PEO) and polyoxyethylene (POE), is an oligomer or polymer of ethylene oxide.

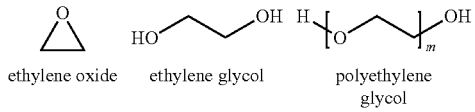

ethylene oxide    ethylene glycol    polyethylene glycol

Polyethylene glycol (PEG) has the chemical formula HO—$(CH_2CH_2O)_m$—H, wherein the index "m" is an integer greater than 1. In simple terms, each polymer molecule has a molecular weight of 18+44(m). However, it is notoriously difficult to prepare a PEG sample with even a moderate value for "m" which is "monodisperse", that is, for which "m" is the same for all polymer molecules in the polymer sample. Instead, a particular sample of PEG will usually have a range of different polymer molecules (each with a different value of "m"), each present in a particular proportion (expressed, e.g., by fraction of total number, by fraction of total weight). The particular population of polymer molecules (i.e., the amounts, by number or weight, of polymer molecules of different molecular weight) gives the polymer sample many of its chemical and physical properties.

Two ways of describing this population of polymer molecules are "number average molecular weight" (Mn) and "weight average molecular weight" (Mw), which are calculated using the following formulae, wherein N and M are respectively the number of, and molecular weight of, each species, i.

$$\overline{M}_n = \left[\frac{\sum_{i=1}^{\infty} N_i M_i}{\sum_{i=1}^{\infty} N_i}\right] \quad \overline{M}_w = \left[\frac{\sum_{i=1}^{\infty} N_i (M_i)^2}{\sum_{i=1}^{\infty} N_i M_i}\right]$$

Mw is always greater than Mn, except when all of the polymer molecules are identical (and the sample is "monodisperse"), in which case Mw equals Mn. The ratio (Mw/Mn) is referred to as the polydispersity index (P), and gives a measure of the breadth of the range of the molecular weights.

In one embodiment, the PEG used in the present invention has a weight average molecular weight (Mw) of from about 200 to about 20,000.

In one embodiment, the range is about 300 to about 20,000.

In one embodiment, the range is about 200 to about 15,000.

In one embodiment, the range is about 300 to about 15,000.

In one embodiment, the range is about 300 to about 10,000.

In one embodiment, the range is about 300 to about 10,000.

In one embodiment, the PEG used in the present invention has a weight average molecular weight (Mw) of from about 200 to about 1,000.

In one embodiment, the range is about 200 to about 800.
In one embodiment, the range is about 300 to about 800.
In one embodiment, the range is about 200 to about 700.
In one embodiment, the range is about 300 to about 700.
In one embodiment, the range is about 200 to about 600.
In one embodiment, the range is about 300 to about 600.
In one embodiment, the range is about 200 to about 500.
In one embodiment, the range is about 300 to about 500.

In one embodiment, the PEG used in the present invention has a weight average molecular weight (Mw) of about 400.

In one embodiment, the PEG used in the present invention has a weight average molecular weight (Mw) of from about 1,000 to about 20,000.

In one embodiment, the range is about 1,000 to about 15,000.

In one embodiment, the range is about 1,000 to about 12,000.

In one embodiment, the range is about 1,000 to about 10,000.

In one embodiment, the range is about 1,000 to about 9,000.

In one embodiment, the range is about 4,000 to about 20,000.

In one embodiment, the range is about 4,000 to about 15,000.

In one embodiment, the range is about 4,000 to about 12,000.

In one embodiment, the range is about 4,000 to about 10,000.

In one embodiment, the range is about 4,000 to about 9,000.

In one embodiment, the range is about 6,000 to about 20,000.

In one embodiment, the range is about 6,000 to about 15,000.

In one embodiment, the range is about 6,000 to about 12,000.

In one embodiment, the range is about 6,000 to about 10,000.

In one embodiment, the range is about 6,000 to about 9,000.

In one embodiment, the range is about 7,000 to about 20,000.

In one embodiment, the range is about 7,000 to about 15,000.

In one embodiment, the range is about 7,000 to about 12,000.

In one embodiment, the range is about 7,000 to about 10,000.

In one embodiment, the range is about 7,000 to about 9,000.

In one embodiment, the PEG used in the present invention has a weight average molecular weight (Mw) of about 8000.

In one embodiment, the PEG used in the present invention is a mixture of two or more PEG polymers with different molecular weight distributions.

One reason for combining PEG polymers with different molecular weight distributions is to achieve a desired viscosity (e.g., of the PEG, of the composition comprising PEG).

In one embodiment, the PEG used in the present invention is a mixture of two or more PEG polymers with different molecular weight distributions, wherein two of said two or more PEG polymers are selected from the PEG polymers described above (e.g., PEG with a weight average molecular weight (Mw) of about 300 to about 800; and PEG with a weight average molecular weight (Mw) of about 6,000 to about 10,000).

In one embodiment, the PEG used in the present invention is a mixture of two or more PEG polymers with different molecular weight distributions, wherein one of said two or more PEG polymers is:

(a) PEG with a weight average molecular weight (Mw) of about 200 to about 1,000; and another of said two or more PEG polymers is:

(b) PEG with a weight average molecular weight (Mw) of about 1,000 to about 20,000.

In one embodiment, the PEG used in the present invention is a mixture of two PEG polymers with different molecular weight distributions.

In one embodiment, the PEG used in the present invention is a mixture of:

(a) PEG with a weight average molecular weight (Mw) of about 200 to about 1,000; and (b) PEG with a weight average molecular weight (Mw) of about 1,000 to about 20,000.

In one embodiment of the above, (a) is PEG with a weight average molecular weight (Mw) of about 200 to about 800.

In one embodiment of the above, (a) is PEG with a weight average molecular weight (Mw) of about 200 to about 700.

In one embodiment of the above, (a) is PEG with a weight average molecular weight (Mw) of about 200 to about 600.

In one embodiment of the above, (a) is PEG with a weight average molecular weight (Mw) of about 200 to about 500.

In one embodiment of the above, (a) is PEG with a weight average molecular weight (Mw) of about 300 to about 1,000.

In one embodiment of the above, (a) is PEG with a weight average molecular weight (Mw) of about 300 to about 800.

In one embodiment of the above, (a) is PEG with a weight average molecular weight (Mw) of about 300 to about 700.

In one embodiment of the above, (a) is PEG with a weight average molecular weight (Mw) of about 300 to about 600.

In one embodiment of the above, (a) is PEG with a weight average molecular weight (Mw) of about 300 to about 500.

In one embodiment of the above, (a) is PEG with a weight average molecular weight (Mw) of about 400.

In one embodiment of the above, (b) is PEG with a weight average molecular weight (Mw) of about 1,000 to about 15,000.

In one embodiment of the above, (b) is PEG with a weight average molecular weight (Mw) of about 1,000 to about 12,000.

In one embodiment of the above, (b) is PEG with a weight average molecular weight (Mw) of about 1,000 to about 10,000.

In one embodiment of the above, (b) is PEG with a weight average molecular weight (Mw) of about 1,000 to about 9,000.

In one embodiment of the above, (b) is PEG with a weight average molecular weight (Mw) of about 4,000 to about 20,000.

In one embodiment of the above, (b) is PEG with a weight average molecular weight (Mw) of about 4,000 to about 15,000.

In one embodiment of the above, (b) is PEG with a weight average molecular weight (Mw) of about 4,000 to about 12,000.

In one embodiment of the above, (b) is PEG with a weight average molecular weight (Mw) of about 4,000 to about 10,000.

In one embodiment of the above, (b) is PEG with a weight average molecular weight (Mw) of about 4,000 to about 9,000.

In one embodiment of the above, (b) is PEG with a weight average molecular weight (Mw) of about 6,000 to about 20,000.

In one embodiment of the above, (b) is PEG with a weight average molecular weight (Mw) of about 6,000 to about 15,000.

In one embodiment of the above, (b) is PEG with a weight average molecular weight (Mw) of about 6,000 to about 12,000.

In one embodiment of the above, (b) is PEG with a weight average molecular weight (Mw) of about 6,000 to about 10,000.

In one embodiment of the above, (b) is PEG with a weight average molecular weight (Mw) of about 6,000 to about 9,000.

In one embodiment of the above, (b) is PEG with a weight average molecular weight (Mw) of about 7,000 to about 20,000.

In one embodiment of the above, (b) is PEG with a weight average molecular weight (Mw) of about 7,000 to about 15,000.

In one embodiment of the above, (b) is PEG with a weight average molecular weight (Mw) of about 7,000 to about 12,000.

In one embodiment of the above, (b) is PEG with a weight average molecular weight (Mw) of about 7,000 to about 10,000.

In one embodiment of the above, (b) is PEG with a weight average molecular weight (Mw) of about 7,000 to about 9,000.

In one embodiment of the above, (b) is PEG with a weight average molecular weight (Mw) of about 8,000.

For example, in one embodiment, the PEG used in the present invention is a mixture of two or more PEG polymers with different molecular weight distributions, wherein one of said two or more PEG polymers is:

(a) PEG with a weight average molecular weight (Mw) of about 200 to about 600; and another of said two or more PEG polymers is:

(b) PEG with a weight average molecular weight (Mw) of about 4,000 to about 12,000.

For example, in one embodiment, the PEG used in the present invention is a mixture of:

(a) PEG with a weight average molecular weight (Mw) of about 200 to about 1,000; and (b) PEG with a weight average molecular weight (Mw) of about 1,000 to about 12,000.

For example, in one embodiment, the PEG used in the present invention is a mixture of:

(a) PEG with a weight average molecular weight (Mw) of about 200 to about 1,000; and (b) PEG with a weight average molecular weight (Mw) of about 1,000 to about 10,000.

For example, in one embodiment, the PEG used in the present invention is a mixture of:

(a) PEG with a weight average molecular weight (Mw) of about 200 to about 600; and (b) PEG with a weight average molecular weight (Mw) of about 4,000 to about 12,000.

For example, in one embodiment, the PEG used in the present invention is a mixture of:

(a) PEG with a weight average molecular weight (Mw) of about 200 to about 600; and (b) PEG with a weight average molecular weight (Mw) of about 6,000 to about 10,000.

For example, in one embodiment, the PEG used in the present invention is a mixture of:

(a) PEG with a weight average molecular weight (Mw) of about 400; and (b) PEG with a weight average molecular weight (Mw) of about 8,000.

In one embodiment, the weight ratio of component (a) to component (b) is about 1:1 to about 20:1 (e.g., from 50 wt % (a) and 50 wt % (b), to 95.25 wt % (a) and 4.75 wt % (b)).

In one embodiment, the range is about 1:1 to about 20:1.
In one embodiment, the range is about 1:1 to about 10:1.
In one embodiment, the range is about 1:1 to about 8:1.
In one embodiment, the range is about 1:1 to about 6:1.
In one embodiment, the range is about 3:1 to about 20:1.
In one embodiment, the range is about 3:1 to about 10:1.
In one embodiment, the range is about 3:1 to about 8:1.
In one embodiment, the range is about 3:1 to about 6:1.
In one embodiment, the range is about 5:1 to about 20:1.
In one embodiment, the range is about 5:1 to about 10:1.
In one embodiment, the range is about 5:1 to about 8:1.
In one embodiment, the range is about 5:1 to about 6:1.

In one embodiment, the weight ratio of component (a) to component (b) is about 5.67:1 (e.g., 85 wt % (a) and 15 wt % (b)).

Composition Comprising PEG

The term "composition comprising PEG", as used herein, refers to a composition comprising PEG that is in a form (e.g., formulation, preparation, medicament) suitable for topical administration (e.g., on and/or around the lips of the patient to be treated).

In one embodiment, the composition comprising PEG contains about 0.1 to 100% PEG, by weight of the overall composition.

In one embodiment, the range is about 1 to 100% PEG by weight.

In one embodiment, the range is about 5 to 100% PEG by weight.

In one embodiment, the range is about 10 to 100% PEG by weight.

In one embodiment, the range is about 20 to 100% PEG by weight.

In one embodiment, the range is about 30 to 100% PEG by weight.

In one embodiment, the range is about 40 to 100% PEG by weight.

In one embodiment, the range is about 50 to 100% PEG by weight.

In one embodiment, the range is about 55 to 100% PEG by weight.

In one embodiment, the range is about 60 to 100% PEG by weight.

In one embodiment, the range is about 65 to 100% PEG by weight.

In one embodiment, the range is about 70 to 100% PEG by weight.

In one embodiment, the range is about 75 to 100% PEG by weight.

In one embodiment, the range is about 80 to 100% PEG by weight.

In one embodiment, the range is about 85 to 100% PEG by weight.

In one embodiment, the range is about 90 to 100% PEG by weight.

In one embodiment, the range is about 91 to 100% PEG by weight.

In one embodiment, the range is about 92 to 100% PEG by weight.

In one embodiment, the range is about 93 to 100% PEG by weight.

In one embodiment, the range is about 94 to 100% PEG by weight.

In one embodiment, the range is about 95 to 100% PEG by weight.

In one embodiment, the range is about 96 to 100% PEG by weight.

In one embodiment, the range is about 97 to 100% PEG by weight.

In one embodiment, the range is about 98 to 100% PEG by weight.

In one embodiment, the range is about 99 to 100% PEG by weight.

In one embodiment, the range is about 1 to 90% PEG by weight.

In one embodiment, the range is about 5 to 90% PEG by weight.

In one embodiment, the range is about 10 to 90% PEG by weight.

In one embodiment, the range is about 20 to 90% PEG by weight.

In one embodiment, the range is about 30 to 90% PEG by weight.

In one embodiment, the range is about 40 to 90% PEG by weight.

In one embodiment, the range is about 50 to 90% PEG by weight.

In one embodiment, the range is about 55 to 90% PEG by weight.

In one embodiment, the range is about 60 to 90% PEG by weight.

In one embodiment, the range is about 65 to 90% PEG by weight.

In one embodiment, the range is about 70 to 90% PEG by weight.

In one embodiment, the range is about 75 to 90% PEG by weight.

In one embodiment, the range is about 80 to 90% PEG by weight.

In one embodiment, the range is about 85 to 90% PEG by weight.

In one embodiment, the range is about 1 to 80% PEG by weight.

In one embodiment, the range is about 5 to 80% PEG by weight.

In one embodiment, the range is about 10 to 80% PEG by weight.

In one embodiment, the range is about 20 to 80% PEG by weight.

In one embodiment, the range is about 30 to 80% PEG by weight.

In one embodiment, the range is about 40 to 80% PEG by weight.

In one embodiment, the range is about 50 to 80% PEG by weight.

In one embodiment, the range is about 55 to 80% PEG by weight.

In one embodiment, the range is about 60 to 80% PEG by weight.

In one embodiment, the range is about 65 to 80% PEG by weight.

In one embodiment, the range is about 70 to 80% PEG by weight.

In one embodiment, the range is about 75 to 80% PEG by weight.

In one embodiment, the composition comprising PEG contains at least about 50% PEG by weight of the overall composition.

In one embodiment, the amount is at least about 60% by weight.

In one embodiment, the amount is at least about 70% by weight.

In one embodiment, the amount is at least about 75% by weight.

In one embodiment, the amount is at least about 80% by weight.

In one embodiment, the amount is at least about 85% by weight.

In one embodiment, the amount is at least about 90% by weight.

In one embodiment, the amount is at least about 91% by weight.

In one embodiment, the amount is at least about 92% by weight.

In one embodiment, the amount is at least about 93% by weight.

In one embodiment, the amount is at least about 94% by weight.

In one embodiment, the amount is at least about 95% by weight.

In one embodiment, the amount is at least about 96% by weight.

In one embodiment, the amount is at least about 97% by weight.

In one embodiment, the amount is at least about 98% by weight.

In one embodiment, the amount is at least about 99% by weight.

In one embodiment, the composition comprising PEG is 100% PEG by weight of the overall composition, In one embodiment, the composition comprising PEG comprises PEG, as described herein, and a pharmaceutically acceptable carrier, diluent, or excipient.

PEG as Lone Active Agent

In one embodiment, the composition comprising PEG is characterized in that it comprises PEG as the lone active agent. Such compositions may be described as specifically excluding any further active agents (i.e., the composition excludes any further active agents; the composition does not further comprise another active agent).

Examples of active agents include antivirals, antibiotics, analgesics, antiseptics, antifungals, and anti-inflammatory agents.

In one embodiment, the composition comprising PEG is characterized in that it comprises PEG as the lone antiviral agent. Such compositions may be described as specifically excluding any further antiviral agents (i.e., the composition excludes any further antiviral agents; the composition does not further comprise another antiviral agent).

In this context, the term "antiviral agent" is used to refer to, and to encompass, both agents for the treatment of, e.g., herpes labialis, herpes genitalis, and herpes zoster, and agents for the treatment of the underlying viral infection, e.g., with HSV-1, HSV-2, and VZV.

In one embodiment, the composition comprising PEG excludes acyclovir, valaciclovir, famciclovir, foscarnet, and penciclovir (i.e., the composition does not further comprise acyclovir, valaciclovir, famciclovir, foscarnet, or penciclovir).

PEG with Additional Active Agents

In one embodiment, the composition comprising PEG further comprises one or more additional active agents (e.g., antivirals, antibiotics, analgesics, antiseptics, antifungals, anti-inflammatory agents).

In one embodiment, the composition comprising PEG further comprises one or more additional antiviral agents.

Again, in this context, the term "antiviral agent" is used to refer to, and to encompass, both agents for the treatment of, e.g., herpes labialis, herpes genitalis, and herpes zoster, and agents for the treatment of the underlying viral infection, e.g., with HSV-1, HSV-2, and VZV.

In one embodiment, the composition comprising PEG further comprises one or more of acyclovir, valaciclovir, famciclovir, foscarnet, and penciclovir.

In one embodiment, the composition comprising PEG further comprises one or more additional active agents other than antivirals (e.g., antibiotics, analgesics, antiseptics, antifungals, anti-inflammatory agents).

Use in Methods of Therapy

One aspect of the present invention pertains to PEG, as described herein, for use in therapy.

One aspect of the present invention pertains to PEG, as described herein, for use in a method of reducing the rate of relapse, delaying relapse, and/or preventing relapse of herpes labialis, herpes genitalis, or herpes zoster by topical administration.

One aspect of the present invention pertains to PEG, as described herein, for use in a method of reducing the rate of relapse of herpes labialis, herpes genitalis, or herpes zoster by topical administration.

One aspect of the present invention pertains to PEG, as described herein, for use in a method of delaying relapse of herpes labialis, herpes genitalis, or herpes zoster by topical administration.

One aspect of the present invention pertains to PEG, as described herein, for use in a method of preventing relapse of herpes labialis, herpes genitalis, or herpes zoster by topical administration.

One aspect of the present invention pertains to PEG, as described herein, for use in a method of reducing the rate of relapse, delaying relapse, and/or preventing relapse of herpes labialis by topical administration.

One aspect of the present invention pertains to PEG, as described herein, for use in a method of reducing the rate of relapse of herpes labialis by topical administration.

One aspect of the present invention pertains to PEG, as described herein, for use in a method of delaying relapse of herpes labialis by topical administration.

One aspect of the present invention pertains to PEG, as described herein, for use in a method of preventing relapse of herpes labialis by topical administration.

One aspect of the present invention pertains to PEG, as described herein, for use in a method of reducing the rate of relapse, delaying relapse, and/or preventing relapse of herpes genitalis by topical administration.

One aspect of the present invention pertains to PEG, as described herein, for use in a method of reducing the rate of relapse of herpes genitalis by topical administration.

One aspect of the present invention pertains to PEG, as described herein, for use in a method of delaying relapse of herpes genitalis by topical administration.

One aspect of the present invention pertains to PEG, as described herein, for use in a method of preventing relapse of herpes genitalis by topical administration.

One aspect of the present invention pertains to PEG, as described herein, for use in a method of reducing the rate of relapse, delaying relapse, and/or preventing relapse of herpes zoster by topical administration.

One aspect of the present invention pertains to PEG, as described herein, for use in a method of reducing the rate of relapse of herpes zoster by topical administration.

One aspect of the present invention pertains to PEG, as described herein, for use in a method of delaying relapse of herpes zoster by topical administration.

One aspect of the present invention pertains to PEG, as described herein, for use in a method of preventing relapse of herpes zoster by topical administration.

Use in the Manufacture of Medicaments

One aspect of the present invention pertains to use of PEG, as described herein, in the manufacture of a medicament for reducing the rate of relapse, delaying relapse, and/or preventing relapse of herpes labialis, herpes genitalis, or herpes zoster by topical administration.

One aspect of the present invention pertains to use of PEG, as described herein, in the manufacture of a medicament for reducing the rate of relapse of herpes labialis, herpes genitalis, or herpes zoster by topical administration.

One aspect of the present invention pertains to use of PEG, as described herein, in the manufacture of a medicament for delaying relapse of herpes labialis, herpes genitalis, or herpes zoster by topical administration.

One aspect of the present invention pertains to use of PEG, as described herein, in the manufacture of a medicament for preventing relapse of herpes labialis, herpes genitalis, or herpes zoster by topical administration.

One aspect of the present invention pertains to use of PEG, as described herein, in the manufacture of a medicament for reducing the rate of relapse, delaying relapse, and/or preventing relapse of herpes labialis.

One aspect of the present invention pertains to use of PEG, as described herein, in the manufacture of a medicament for reducing the rate of relapse of herpes labialis by topical administration.

One aspect of the present invention pertains to use of PEG, as described herein, in the manufacture of a medicament for delaying relapse of herpes labialis by topical administration.

One aspect of the present invention pertains to use of PEG, as described herein, in the manufacture of a medicament for preventing relapse of herpes labialis by topical administration.

One aspect of the present invention pertains to use of PEG, as described herein, in the manufacture of a medicament for reducing the rate of relapse, delaying relapse, and/or preventing relapse of herpes genitalis by topical administration.

One aspect of the present invention pertains to use of PEG, as described herein, in the manufacture of a medicament for reducing the rate of relapse of herpes genitalis by topical administration.

One aspect of the present invention pertains to use of PEG, as described herein, in the manufacture of a medicament for delaying relapse of herpes genitalis by topical administration.

One aspect of the present invention pertains to use of PEG, as described herein, in the manufacture of a medicament for preventing relapse of herpes genitalis by topical administration.

One aspect of the present invention pertains to use of PEG, as described herein, in the manufacture of a medicament for reducing the rate of relapse, delaying relapse, and/or preventing relapse of herpes zoster by topical administration.

One aspect of the present invention pertains to use of PEG, as described herein, in the manufacture of a medicament for reducing the rate of relapse of herpes zoster by topical administration.

One aspect of the present invention pertains to use of PEG, as described herein, in the manufacture of a medicament for delaying relapse of herpes zoster by topical administration.

One aspect of the present invention pertains to use of PEG, as described herein, in the manufacture of a medicament for preventing relapse of herpes zoster by topical administration.

Methods of Therapy

One aspect of the present invention pertains to a method of reducing the rate of relapse, delaying relapse, and/or preventing relapse of herpes labialis, herpes genitalis, or herpes zoster in a patient, comprising topically administering to said patient a therapeutically effective amount of: PEG or a composition comprising PEG, as described herein.

One aspect of the present invention pertains to a method of reducing the rate of relapse, delaying relapse, and/or preventing relapse of herpes labialis in a patient, comprising topically administering to said patient a therapeutically effective amount of: PEG or a composition comprising PEG, as described herein.

One aspect of the present invention pertains to a method of reducing the rate of relapse of herpes labialis in a patient, comprising topically administering to said patient a therapeutically effective amount of: PEG or a composition comprising PEG, as described herein.

One aspect of the present invention pertains to a method of delaying relapse of herpes labialis in a patient, comprising topically administering to said patient a therapeutically effective amount of: PEG or a composition comprising PEG, as described herein.

One aspect of the present invention pertains to a method of preventing relapse of herpes labialis in a patient, comprising topically administering to said patient a therapeutically effective amount of: PEG or a composition comprising PEG, as described herein.

One aspect of the present invention pertains to a method of reducing the rate of relapse, delaying relapse, and/or preventing relapse of herpes genitalis in a patient, comprising topically administering to said patient a therapeutically effective amount of: PEG or a composition comprising PEG, as described herein.

One aspect of the present invention pertains to a method of reducing the rate of relapse of herpes genitalis in a patient, comprising topically administering to said patient a therapeutically effective amount of: PEG or a composition comprising PEG, as described herein.

One aspect of the present invention pertains to a method of delaying relapse of herpes genitalis in a patient, comprising topically administering to said patient a therapeutically effective amount of: PEG or a composition comprising PEG, as described herein.

One aspect of the present invention pertains to a method of preventing relapse of herpes genitalis in a patient, comprising topically administering to said patient a therapeutically effective amount of: PEG or a composition comprising PEG, as described herein.

One aspect of the present invention pertains to a method of reducing the rate of relapse, delaying relapse, and/or preventing relapse of herpes zoster in a patient, comprising topically administering to said patient a therapeutically effective amount of: PEG or a composition comprising PEG, as described herein.

One aspect of the present invention pertains to a method of reducing the rate of relapse of herpes zoster in a patient, comprising topically administering to said patient a therapeutically effective amount of: PEG or a composition comprising PEG, as described herein.

One aspect of the present invention pertains to a method of delaying relapse of herpes zoster in a patient, comprising topically administering to said patient a therapeutically effective amount of: PEG or a composition comprising PEG, as described herein.

One aspect of the present invention pertains to a method of preventing relapse of herpes zoster in a patient, comprising topically administering to said patient a therapeutically effective amount of: PEG or a composition comprising PEG, as described herein.

Disorders Treated

Again, for the avoidance of doubt, it is not asserted that the methods described herein prevent viral infection (e.g., prevent infection with HSV-1, HSV-2, or VZV). Instead, the methods described herein are useful in therapy for diseases and disorders associated with, triggered by, or caused by, viral infection (i.e., diseases and disorders associated with, triggered by, or caused by, HSV-1, HSV-2, or VZV infection). In this way, the methods described herein may be described as palliative care, in the sense of preventing and/or relieving the symptoms of viral infection (e.g., HSV-1, HSV-2, or VZV infection).

The methods described herein are particularly useful in therapies for herpes labialis (also referred to as oral herpes), herpes genitalis (also referred to as genital herpes), and herpes zoster (also referred to as shingles and zona).

The methods described herein are especially useful in therapies for herpes labialis (also referred to as oral herpes), e.g., recurrent herpes labialis.

In one embodiment (e.g., of use in methods of therapy, of use in the manufacture of medicaments, of methods of therapy), the treatment is: reducing the rate of relapse of herpes labialis.

In one embodiment (e.g., of use in methods of therapy, of use in the manufacture of medicaments, of methods of therapy), the treatment is: delaying relapse of herpes labialis.

In one embodiment (e.g., of use in methods of therapy, of use in the manufacture of medicaments, of methods of therapy), the treatment is: preventing relapse of herpes labialis.

The term "relapse" of a disease or disorder (e.g., herpes labialis, herpes genitalis, herpes zoster) is used herein in the conventional sense to refer to recurrence of that disease or disorder, e.g., recurrence of signs and symptoms of that disease or disorder.

The term "relapse of herpes labialis" is used herein in the conventional sense to refer to recurrence of herpes labialis, e.g., recurrence of herpes labialis signs and symptoms, such as erythema, papule, vesicle, ulceration, erosion, swelling, etc.

Both the herpes simplex viruses (HSV-1 and HSV-2) and the varicella zoster virus (VZV) belong to the same viral subfamily (alphaherpesvirinae). Consequently, the compositions and methods described herein may also be useful in the treatment and/or prevention of other HSV-1, HSV-2, and VZV disorders, including herpetic whitlow, herpetic gingivostomatitis, herpes gladiatorum, herpetic keratoconjunctivitis, herpesviral encephalitis, herpeviral meningitis, neonatal herpes simplex, herpetic sycosis, and eczema herpeticum.

Therapeutically-Effective Amount

The term "therapeutically-effective amount," as used herein, pertains to that amount of PEG or a composition comprising PEG, which is effective for producing some desired therapeutic effect, commensurate with a reasonable benefit/risk ratio, when administered in accordance with a desired treatment regimen.

Routes of Administration

The PEG or composition comprising PEG, as described herein, is administered topically.

The term "topical administration" is used in its broadest sense to include administration to a surface on the body that is generally open to the surroundings. This includes not only the skin but also the nasal and oral passages and the genitalia. Thus, topical administration can include application to the skin, application to the nasal passages, application to the oral cavity (including the upper throat), and application to the genitalia (e.g., in connection with therapy for herpes genitalis).

In one embodiment, the PEG or composition comprising PEG, as described herein, is administered topically to one or more sites exhibiting an active viral infection (for example, a cold sore or other physical symptom of a "breakout" indicative of an active viral infection) or to a site where there are no signs of an active infection but where active infection (e.g., recurrent breakouts) is known to occur, or is expected to occur.

In one embodiment, the PEG or composition comprising PEG, as described herein, is administered topically, on and/or around the lips of the patient to be treated (e.g., in connection with therapy for herpes labialis).

In one embodiment, the PEG or composition comprising PEG, as described herein, is administered topically, on (e.g., at least a part of; substantially all of; all of) the lips and the surrounding facial skin (e.g., <1 cm from the border of the lips) of the patient to be treated (e.g., in connection with therapy for herpes labialis).

For example, in one embodiment, the PEG or composition comprising PEG, as described herein, is administered topically, on at least a part of: the lips and the surrounding facial skin <1 cm from the border of the lips of the patient to be treated (e.g., in connection with therapy for herpes labialis).

In one embodiment, the PEG or composition comprising PEG, as described herein, is administered topically, on the whole of both lips of the patient to be treated (e.g., in connection with therapy for herpes labialis).

In one embodiment, the PEG or composition comprising PEG, as described herein, is administered topically, on the whole of both lips and on the surrounding facial skin of the patient to be treated (e.g., in connection with therapy for herpes labialis).

In one embodiment, the PEG or composition comprising PEG, as described herein, is administered topically, on (e.g., at least a part of; substantially all of; all of) the genitalia and the surrounding skin (e.g., the pubic area and/or the groin area) of the patient to be treated (e.g., in connection with therapy for herpes genitalis).

Rate of Administration

The PEG or composition comprising PEG, as described herein, may be administered according to any appropriate therapeutic regimen.

For example, the PEG or composition comprising PEG may be administered from once daily to five times daily, for example, once daily, twice daily, three times daily, etc. In a preferred embodiment, the PEG or composition comprising PEG is administered twice daily.

If, during therapy, a relapse occurs, then, for the duration of the relapse, the PEG or composition comprising PEG may optionally be administered from 1 to 10 times daily. For example, the PEG or composition comprising PEG may be administered from 3 to 7 times daily during relapse. In a preferred embodiment, the PEG or composition comprising PEG is administered 5 times daily during relapse.

Duration of Therapy

In many respects, the PEG or composition comprising PEG, as described herein, acts as a prophylatic, in that it acts to reduce the rate of relapse, delay relapse, and/or prevent relapse, for example, of herpes labialis, herpes genitalis, or herpes zoster.

Consequently, the PEG or composition comprising PEG, as described herein, may be administered for a prolonged period of time (referred to herein as the administration period), and if desired, indefinitely.

For example, the PEG or composition comprising PEG, as described herein, may be administered (e.g., once daily, twice daily, three times daily, etc.) for a period (e.g., an administration period) of at least 4 weeks.

In one embodiment, the administration period is at least 6 weeks.

In one embodiment, the administration period is at least 8 weeks.

In one embodiment, the administration period is at least 10 weeks.

In one embodiment, the administration period is at least 3 months.

In one embodiment, the administration period is at least 4 months.

In one embodiment, the administration period is at least 6 months.

In one embodiment, the administration period is at least 8 months.

In one embodiment, the administration period is at least 1 year.

In one embodiment, the administration period is at least 2 years.

In one embodiment, the administration period is 4 weeks to 1 year.

In one embodiment, the administration period is 6 weeks to 1 year.

In one embodiment, the administration period is 8 weeks to 1 year.

In one embodiment, the administration period is 10 weeks to 1 year.

In one embodiment, the administration period is 3 months to 1 year.

In one embodiment, the administration period is 4 months to 1 year.

In one embodiment, the administration period is 6 months to 1 year.

In one embodiment, the administration period is 6 months to 2 years.

In one embodiment, the administration period is 8 months to 2 years.

In one embodiment, the administration period is 1 year to 2 years.

For example, as therapy for recurrent herpes labialis, the PEG or composition comprising PEG, as described herein, may be administered twice daily, to the whole of both lips and the surrounding facial skin <1 cm from the border of the lips, for a period (e.g., an administration period), indefinitely, in order to reduce the rate of relapse, delay relapse, and/or prevent relapse.

Alternatively, the therapy may interrupted by any number of rest periods. For example, therapy may proceed for a first administration period, then discontinued for a first rest period, then resumed for a second administration period, then discontinued for a second rest period, etc., wherein each administration period may be the same or different length, and each rest period may be the same or different length.

Separately, the start of therapy is not necessarily associated with any clinical event. For example, it is not a requirement that therapy be started in the early prodromal phase, before symptoms of the acute condition appear. Instead, therapy may be started at any time, and preferably before a relapse occurs (e.g., before the prodromal phase, before acute symptoms appear, etc.).

Dosage

It will be appreciated by one of skill in the art that appropriate dosages of PEG or composition comprising PEG can vary from patient to patient. Determining the optimal dosage will generally involve the balancing of the level of therapeutic benefit against any risk or deleterious side effects. The selected dosage level will depend on a variety of factors including, but not limited to, the time of administration, the duration of the treatment, other drugs, compounds, and/or materials used in combination, the severity of the disorder, and the species, sex, age, weight, condition, general health, and prior medical history of the patient. The amount of PEG or composition comprising PEG will ultimately be at the discretion of the physician, veterinarian, or clinician, although generally the dosage will be selected to achieve local concentrations at the site of action which achieve the desired effect without causing substantial harmful or deleterious side-effects.

In general, a suitable dose of PEG is in the range of about 0.02 to 2 g, more typically about 0.05 to 0.5 g, for example, about 0.2 g, per administration.

The Subject/Patient

The subject/patient may be a mammal, preferably a human, for example, a male human or a female human.

In one embodiment, the subject/patient is a human already infected with HSV-1, HSV-2, and/or VZV.

In one embodiment, the subject/patient is a human already infected with HSV-1 and/or HSV-2.

In one embodiment, the subject/patient is a human already infected with VZV.

In one embodiment, the subject/patient is a human which has suffered from and/or is suffering from, herpes labialis, herpes genitalis, or herpes zoster.

In one embodiment, the subject/patient is a human which has suffered from and/or is suffering from, herpes labialis, i.e., suffers from, or may be expected to suffer from, recurrent herpes labialis.

In one embodiment, the subject/patient is a human which has suffered from and/or is suffering from, herpes genitalis, i.e., suffers from, or may be expected to suffer from, recurrent herpes genitalis.

In one embodiment, the subject/patient is a human which has suffered from and/or is suffering from, herpes zoster, i.e., suffers from, or may be expected to suffer from, recurrent herpes zoster.

In one embodiment, the subject/patient is a human at risk of a relapse of herpes labialis, herpes genitalis, or herpes zoster.

In one embodiment, the subject/patient is a human at risk of a relapse of herpes labialis.

In one embodiment, the subject/patient is a human at risk of a relapse of herpes genitalis.

In one embodiment, the subject/patient is a human at risk of a relapse of herpes zoster.

Combination Therapies

The therapies described herein may be used alone or as part of a combination therapy, in which two or more therapeutic modalities are combined, for example, sequentially or simultaneously. For example, PEG or a composition comprising PEG, as described herein, may also be used in combination therapies, e.g., in conjunction with other agents. Examples of additional treatments and therapies include, but are not limited to, treatment with one or more of acyclovir, valaciclovir, famciclovir, foscarnet, and penciclovir.

One aspect of the present invention pertains to use of PEG, in combination with one or more (e.g., 1, 2, 3, 4, etc.) additional therapeutic agents. The particular combination would be at the discretion of the physician who would select dosages using his common general knowledge and dosing regimens known to a skilled practitioner.

The agents (i.e., PEG or a composition comprising PEG, as described herein, plus one or more other agents) may be administered simultaneously or sequentially, and may be administered in individually varying dose schedules and via different routes.

The agents (i.e., PEG or a composition comprising PEG, as described here, plus one or more other agents) may be formulated together in a single dosage form, or alternatively, the individual agents may be formulated separately and presented together in the form of a kit, optionally with instructions for their use.

Kits

One aspect of the invention pertains to a kit comprising (a) PEG or a composition comprising PEG, as described herein, e.g., preferably provided in a suitable container and/or with suitable packaging; and (b) instructions for use, e.g., written instructions on how to administer the PEG or composition comprising PEG.

The written instructions may also include a list of indications for which the active ingredient is a suitable treatment.

Formulations

While it is possible for the PEG to be administered alone, it may be preferable to present it as a pharmaceutical formulation (e.g., composition, preparation, medicament) comprising PEG together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, sweetening agents, essential oils, and moisturizers. The formulation may further comprise other active agents, for example, other therapeutic or prophylactic agents.

However, in one embodiment, the composition comprising PEG, as described herein, is characterized in that it comprises PEG as the lone active agent. Such formulations may be described as specifically excluding any further active agents. In another embodiment, the composition comprising PEG, as described herein, is characterized in that it comprises PEG as the lone antiviral agent. Such formulations may be described as specifically excluding any further a agents.

Alternatively, in one embodiment, the composition comprising PEG, as described herein, is characterized in that it further comprises one or more additional antiviral agents, for example, one or more of acyclovir, valaciclovir, famciclovir, foscamet, and penciclovir. Furthermore, in one embodiment, the composition comprising PEG, as described herein, is characterized in that it further comprises one or more additional active agents, such as antibiotics, analgesics, antiseptics, antifungals, and anti-inflammatory agents.

In one embodiment, the composition comprising PEG is essentially water-free (i.e., comprises PEG but substantially no water).

In one embodiment, the composition comprising PEG contains less than 5% water, by weight of the overall formulation.

In one embodiment, the composition comprising PEG contains less than 1% water, by weight of the overall formulation.

In one embodiment, the composition comprising PEG further comprises water (i.e., comprises both PEG and water) (e.g., 1 to 20%, 1 to 10%, 1 to 5% water, by weight of the overall formulation).

Thus, in one embodiment, the composition comprises:
(a) polyethylene glycol, as described herein; and
(b) water.

In one embodiment, the composition comprising PEG contains 1 to 20% water, by weight of the overall formulation.

In one embodiment, the composition comprising PEG contains 1 to 10% water, by weight of the overall formulation.

In one embodiment, the composition comprising PEG contains 1 to 5% water, by weight of the overall formulation.

Typically, the composition comprising PEG comprises from about 1% to about 100% PEG, by weight of the overall formulation.

In other embodiments, the range is from about 20% to about 100%, or from about 50% to about 100%, or from about 70% to about 100%, or from about 80% to about 100%, by weight of the overall formulation.

In other embodiments, the range is from about 20% to about 90%, or from about 50% to about 90%, or from about 70% to about 90%, or from about 80% to about 90%, by weight of the overall formulation.

In one embodiment, the composition comprising PEG consists essentially of PEG.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, drops, tinctures, gels, pastes, ointments, creams, lotions, oils, balms, sticks, facemasks, foams, sprays, mists, aerosols, wipes (e.g., as provided on a solid carrier), or patches (e.g., as provided on a solid carrier, with an adhesive).

Formulations (especially water-containing formulations) may additionally comprise one or more preservatives to maintain shelf-life of the product. However, non-water based formulations may often be prepared without the need to include preservatives, which reduces cost, simplifies the formulation, and eliminates the possibility of adverse reactions by users.

Many viral infections, particularly recurring infections, are susceptible to UV-stimulated breakouts (i.e., breakouts stimulated by exposure to sunlight). Accordingly, the addition of UV filters to the formulations can be particularly useful for further reducing or preventing breakouts.

Consequently, the formulation may further comprise one or more sunscreen components, as described herein, for example, at least one UVA filter substance and/or at least one UVB filter substance and/or at least one inorganic pigment.

The UVB filters may be, for example, oil-soluble or water-soluble. Examples of oil-soluble UVB filters include: 3-benzylidenecamphor and derivatives thereof, e.g., 3-(4-methylbenzylidene)camphor; 4-aminobenzoic acid derivatives, preferably 2-ethylhexyl 4-(dimethylamino)benzoate, amyl 4-(dimethylamino)benzoate; esters of cinnamic acid, preferably 2-ethylhexyl 4-methoxycinnamate, isopentyl 4-methoxycinnamate; esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di(2-ethylhexyl) 4-methoxybenzalmalonate; and 2,4,6-trianilino(p-carbo-2'-ethyl-1'-hexyloxy)-1,3,5-triazine.

Examples of water-soluble UVB filters include: 2-phenylbenzimidazole-5-sulfonic acid and salts thereof, e.g., sodium, potassium or triethanolammonium salts; sulfonic acid derivatives of benzophenones, preferably 2-hydroxy-4-methoxybenzophenone-5-sulfonic acid and its salts; and sulfonic acid derivatives of 3-benzylidenecamphor, such as, for example, 4-(2-oxo-3-bornylidenemethyl)benzenesulfonic acid, 2-methyl-5-(2-oxo-3-bornylipenemethyl)sulfonic acid and its salts.

The UVA filters may be, for example, selected from: derivatives of dibenzoylmethane, in particular 1-(4'-tert-butylphenyl)-3-(4'-methoxyphenyl) propane-1,3-dione and 1-phenyl-3-(4'-isopropylphenyl)propane-1,3-dione.

Additional examples of UV filters include p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naptholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxysubstituted benzophenones; uric and vilouric acids; tannic acid and its derivatives; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone), dibenzoylmethane derivatives, avobenzone, 4-isopropyldibenzoylmethane, butylmethoxydibenzoylmethane, 4-isopropyl-dibenzoylmethane, octocrylene, and drometrizole trisiloxane.

Additional examples of UV filters include N,N,N-trimethyl-4-(2-oxoborn-3-ylidenemethyl)anilinium methyl sulphate; homosalate (INN); oxybenzone (INN); 2-phenylbenzimidazole-5-sulphonic acid or a potassium, sodium or triethanolamine salt thereof; 3,3'-(1,4-phenylenedimethylene)bis(7,7-dimethyl-2-oxobicyclo-[2,2,1]hept-1-yl-methanesulfonic acid) or a salt thereof; 1-(4-tert-butylphenyl)-3-(4-methoxyphenyl)propane-1,3-dione; alpha-(2-oxoborn-3-ylidene)-toluene-4-sulphonic acid or a salt thereof; 2-cyano-3,3-diphenyl acrylic acid, 2-ethylhexyl ester (octocrylene); a polymer of N-{(2 and 4)-[(2-oxoborn-3-ylidene)methyl]benzyl}acrylamide; octyl methoxycinnamate; ethoxylated ethyl-4-aminobenzoate (PEG-25 PABA); isopentyl-4-methoxycinnamate (isoamyl p-methoxycinnamate); 2,4,6-trianilino-(p-carbo-2'-ethylhexyl-1'-oxy)-1,3,5-triazine (octyl triazone); phenol, 2-(2H-benzotriazol-2-yl)-4-methyl-6-(2-methyl-3-(1,3,3,3-tetramethyl-1-(trimethylsilyl)oxy)-disiloxanyl)propyl) (drometrizole trisiloxane); benzoic acid, 4,4-((6-(((1,1-dimethylethyl)amino)carbonyl)phenyl)amino)-1,3,5-triazine-2,4-diyl)diimino)bis-, bis-(2-ethylhexyl)ester); 3-(4'-methylbenxylidene)-d-1 camphor (4-methylbenzylidene camphor); 3-benzylidene camphor (3-benzylidene camphor); 2-ethylhexyl salicylate (octyl-salicylate); 4-dimethyl-amino-benzoate of ethyl-2-hexyl (octyl dimethyl PABA); 2-hydroxy-4-methoxybenzophenone-5-sulfonic acid (benzophenone-5) or the sodium salt thereof; 2,2'-methylene-bis-6-(2H-benzotriazol-2yl)-4-(tetramethylbutyl)-1,1,3,3-phenol; monosodium salt of 2,2'-bis-(1,4-phenylene)-1H-benzimidazole-4,6-disulphonic acid); (1,3,5)-triazine-2,4-bis((4-(2-ethylhexyloxy)-2-hydroxy)-phenyl)-6-(4-methoxyphenyl); dimethicodiethylbenzalmalonate (CAS No 207574-74-1); titanium dioxide; and benzoic acid, 2-[4-(diethylamino)-2-hydroxybenzoyl], hexylester (diethylamino hydroxybenzoyl hexyl benzoate; CAS No 302776-68-7).

Examples of inorganic pigments which are customarily used in cosmetics for protecting the skin against UV rays include oxides of titanium, zinc, iron, zirconium, silicon, manganese, aluminium, cerium, and mixtures thereof.

The formulation may additionally comprise one or more antioxidants, as described herein. The antioxidants may, for example, be selected from: amino acids (for example, glycine, histidine, tyrosine, tryptophan) and derivatives thereof, imidazoles (for example, urocanic acid) and derivatives thereof, peptides, such as D,L-carnosine, D-carnosine, L-carnosine and derivatives thereof (for example anserine), carotenoids, carotenes (for example α-carotene, γ-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine buthionine sulphones, penta-, hexa- and heptathionine-sulphoximine) in very low tolerated doses (for example pmol to pmol/kg), and furthermore (metal) chelating agents (for example, α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example, γ-linolenic acid, linoleic acid, oleic acid), folic acid and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (for example, ZnO, ZnSO$_4$), selenium and derivatives thereof (for example, selenium methionine), stilbenes and derivatives thereof (for example, stilbene oxide, trans-stilbene oxide) and the derivatives of these active ingredients mentioned which are suitable according to the invention (salts, esters, ethers, sugars, nucleotides, nucleosides, peptides and lipids).

In one embodiment, the formulation comprises:
(a) polyethylene glycol, as described herein; and
(b) none or one or more pharmaceutically acceptable carriers, diluents, and excipients.

In one embodiment, the formulation comprises:
(a) polyethylene glycol, as described herein; and
(b) none or one or more pharmaceutically acceptable carriers, diluents, excipients, adjuvants, fillers, buffers, preservatives, anti-oxidants, lubricants, stabilisers, solubilisers, surfactants, masking agents, colouring agents, flavouring agents, sweetening agents, essential oils, and moisturizers.

In one embodiment, the formulation comprises:
(a) polyethylene glycol, as described herein; and
(b) one or more sunscreen components.

In one embodiment, the formulation comprises:
(a) polyethylene glycol, as described herein;
(b) one or more sunscreen components; and
(c) none or one or more pharmaceutically acceptable carriers, diluents, and excipients.

In one embodiment, the formulation comprises:
(a) polyethylene glycol, as described herein;
(b) one or more sunscreen components; and
(c) none or one or more pharmaceutically acceptable carriers, diluents, excipients, adjuvants, fillers, buffers, preservatives, anti-oxidants, lubricants, stabilisers, solubilisers, surfactants, masking agents, colouring agents, flavouring agents, sweetening agents, essential oils, and moisturizers.

In one embodiment, the formulation comprises:
(a) polyethylene glycol, as described herein;
(b) one or more sunscreen components; and
(c) water.

In one embodiment, the formulation comprises:
(a) polyethylene glycol, as described herein;
(b) one or more sunscreen components;
(c) water; and
(d) none or one or more pharmaceutically acceptable carriers, diluents, and excipients.

In one embodiment, the formulation comprises:
(a) polyethylene glycol, as described herein;
(b) one or more sunscreen components;
(c) water; and
(d) none or one or more pharmaceutically acceptable carriers, diluents, excipients, adjuvants, fillers, buffers, preservatives, anti-oxidants, lubricants, stabilisers, solubilisers, surfactants, masking agents, colouring agents, flavouring agents, sweetening agents, essential oils, and moisturizers.

Gel Formulations

In one embodiment, the formulation is a composition in the form of a gel.

Gels typically are formed by placing a gelling agent (the dispersed phase) in a solvent (the continuous phase) to produce a viscous, jellylike product. For example, 2% gelatin in water is known to form a stiff gel. Such gels are typically made by cooling a solution of the gelling agent in the solvent so that the gelling agent forms submicroscopic crystalline particle groups that retain much solvent in the interstices.

The gel formulations comprise PEG, as described herein. In one embodiment, the gel formulation comprises PEG, as described herein, in concentrations of about 0.1% to about 100% by weight based on the overall weight of the gel formulation. In other embodiments, the range is about 50% to about 100% by weight, or about 60% to about 100% by weight, or about 70% to about 100% by weight, or about 80% to about 100% by weight, or about 90% to about 100% by weight, based on the overall weight of the gel formulation.

The gel may additionally comprise one or more thickeners or gel forming agents, as described herein. Examples of suitable gel forming agents include cellulose ethers, such as methyl cellulose, hydroxyethyl cellulose, or carboxymethyl cellulose, and vegetable hydrocolloids, such as sodium alginate, tragacanth, or gum arabic.

The gel may additionally comprise one or more solvents, for example, one or more polyols, as described herein. Examples of polyols suitable for use as co-solvents include ethylene glycol, propylene glycol, glycerin, pentaerythritol, 1,2-propanediol, dimethylpolysilanol, monomethyl ether, monoethyl ether, monobutyl ether, and diethylene glycol.

The gel may additionally comprise one or more non-aqueous solvents, as described herein. Examples of suitable non-aqueous solvents include lower alkyl alcohols (particularly C1-C6 alcohols), pyrrolidones, and volatile silicones; for example, methanol, ethanol, isopropyl alcohol, ethoxydiglycol, 1-methyl-2-pyrrolidone, polydimethylsiloxane, polyorganosiloxanes, and other silicone polymers.

Gels are particularly useful for delivery of the PEG or composition comprising PEG to the site of an active breakout arising from a viral infection. For example, gels can be applied to cold sores around the mouth of a user, as well as on and around skin breakouts symptomatic of viral infection. Moreover, such gels can be applied prior to active breakouts to prevent formation of sores.

Water-based gels are disadvantageous in certain applications because they are freely whisked away by bodily fluids (e.g., saliva) or external aqueous fluids (e.g., mouth medications solubilized by beverages). Non-water based gels are often beneficial in that they remain on the application site longer and thus allow for prolonged activity at the site of application.

Non-water based gels are particularly beneficial in that they provide an occlusive effect. As pointed out above, water-based gels are plagued by the evaporative effect (i.e., the water solvent evaporates quickly allowing the remaining components to be easily whisked away). In the non-water based gels, however, the absence of the water solvent significantly reduces or completely eliminates the evaporative effect. Rather, an occlusive effect is observed, and the active components of the gel are held in contact with the skin for a prolonged period of time to increase the effectiveness of the gel.

Preferably, the gel has a viscosity in the range of about 1 cP to about 30,000 cP, for example about 100 cP to about 20,000 cP, measured at 25° C. As necessary or desired, the viscosity of the gel can be adjusted by the addition of other components, e.g., water, thickeners, etc., as described herein.

The gel may additionally comprise one or more components useful for making them more compatible and non-irritating to the mucus membranes of the nasal passages. Thus, in one embodiment, the formulation is a composition in the form of a nose gel (i.e., a gel that is suited for use in the nose or nasal passages of a mammal. For example, nose gels preferably include one or more electrolytes useful for increasing the salinity of the nose gel. Bodily fluids, including those bathing the mucous membranes of the nasal passages, have a specific electrolyte balance and altering such electrolyte balance can cause irritating effects. Thus, nose gels preferably include one or more salt components in concentrations useful to maintain the natural electrolyte balance of the mucous membranes within the nasal passages. In some embodiments, the nose gel compositions comprise sodium chloride.

The gel may additionally comprise one or more further components, such as penetration enhancers, humectants, emulsifiers, oils, fats, paraffins, thickeners, solubilizers, acids, and bases. Examples of further components include polycarbophil, polyacrylic acid, polyacrylates, polyvinylpyrrolidone, and alkyl celluloses (such as methyl cellulose, ethyl cellulose, propyl cellulose, or butyl cellulose).

In one embodiment, the formulation is the form of a gel (e.g., nose spray, throat spray) comprising:
(a) polyethylene glycol, as described herein;
(b) none or one or more thickeners or gel forming agents;

(c) none or some water;
(d) none or one or more other solvents (other than water);
(e) none or one or more electrolytes useful for increasing salinity of the gel;
(f) none or one or more penetration enhancers;
(g) none or one or more preservatives;
(h) none or one or more colouring agents; and
(i) none or one or more flavourants.

Spray Formulations

In one embodiment, the formulation is a composition in the form of a spray, for example, a nose spray or a throat spray.

Such formulations are particularly useful for delivery of the composition comprising PEG to the areas of the body for which application of a topical gel may not be convenient or as effective. A nose spray is understood to refer to a spray composition amenable to spraying into one or both nostrils of a mammal and safe for contact with the mucous membranes within the nasal passages. A throat spray is understood to refer to a spray composition amenable to spraying into the mouth of a mammal and safe for contact with all surfaces of the mouth and throat. In general, a throat spray is intended to predominately by-pass the mouth of the user (i.e., the majority of the spray does not necessarily contact the tongue, palate, or interior cheek surfaces) and be applied to the throat area generally.

The spray formulations comprise PEG, as described herein. In one embodiment, the spray formulation comprises PEG, as described herein, in concentrations of about 0.1% to about 100% by weight based on the overall weight of the spray formulation. In other embodiments, the range is about 50% to about 100% by weight, or about 60% to about 100% by weight, or about 70% to about 100% by weight, or about 80% to about 100% by weight, or about 90% to about 100% by weight, based on the overall weight of the spray formulation.

In certain embodiments, the spray formulations further comprise one or more polyols. Polyols, such as glycerol, are particularly useful in light of their water-binding effect. As used herein, the term "polyol" is intended to refer to any organic compound containing two or more hydroxyl groups, and includes, for example, polymers and monomers with hydroxyl functional groups available for organic reactions. Examples of suitable polyols include ethylene glycol, propylene glycol, glycerin, pentaerythritol, 1,2-propanediol, dimethylpolysilanol, ethylene glycol monomethyl ether, ethylene glycol monoethyl ether, ethylene glycol monobutyl ether, and diethylene glycol. The one or more polyols may be included in the spray formulation in concentrations in the range of about 0.1% to about 30% by weight, about 1% to about 30% by weight, about 5% to about 30% by weight, or about 5% to about 20% by weight.

The spray formulations are preferably water-based formulations which comprise at least one aqueous solvent. In one embodiment, the spray formulations comprise water as the major solvent. However, other solvents (e.g., alcohols) may also be used.

The spray formulations may further comprise other components, for example, components useful for preparing a formulation amenable to nose or throat application. For example, the spray formulations can include preservatives, colouring agents, penetration enhancers, flavorants, and the like. The spray formulations can include additional components, such as carriers, acids, bases, and the like.

In one embodiment, the formulation is the form of a spray (e.g., nose spray, throat spray) comprising:

(a) polyethylene glycol, as described herein;
(b) none or one or more other polyols (other than polyethylene glycol);
(c) none or some water;
(d) none or one or more other solvents (other than water) (e.g., alcohols);
(e) none or one or more preservatives;
(f) none or one or more colouring agents;
(g) none or one or more penetration enhancers; and
(g) none or one or more flavourants.

Balm Formulations

In one embodiment, the formulation is a composition in the form of a balm, for example, a balm which is suited for use on or around the lips of a mammal (e.g., a lipbalm).

In one embodiment, the balm is provided in the form of a stick (e.g., a lipstick).

The balm may be, for example, a cosmetic, such as a lipstick or a lip gloss. The balm may be colored (e.g., a colored lipstick) or may be essentially colorless. The balm may or may not include a scent or a flavoring agent.

The balm formulations comprise PEG, as described herein. In one embodiment, the balm formulation comprises PEG, as described herein, in concentrations of about 0.1% to about 90% by weight based on the overall weight of the balm formulation. In other embodiments, the range is about 50% to about 90% by weight, or about 60% to about 90% by weight, or about 70% to about 90% by weight, based on the overall weight of the balm formulation.

The balm formulations generally comprise one or more base forming components that comprise the bulk of the balm. For example, solid sticks can comprise natural or synthetic waxes, fatty alcohols, or fatty acid esters as the base forming component. Specific examples of bases which are suitable for use in balms are liquid oils (e.g., paraffin oils, castor oil, cetosearyl alcohol, and isopropyl myristate), semisolid constituents (e.g., vaseline and lanolin), solid constituents (e.g., beeswax, ceresine and microcrystalline waxes and ozokerite), and high-melting waxes (e.g., carnauba wax and candelilla wax). All of the foregoing base forming components may be described, as a group, by the phrase "waxy components". Thus, as used in relation to a balm, a waxy component is any of the noted materials that can be used to form the bulk of the balm and, like waxes, are generally solid or semi-solid at ambient temperature but are at least softened at temperatures approaching the average human body temperature (i.e., about 37° C.).

In a preferred embodiment, the balm further comprises one or more sunscreen components, as described herein, for example, at least one UVA filter substance and/or at least one UVB filter substance and/or at least one inorganic pigment, as described herein.

Examples of other components that may be included in the balms include pigments and other colouring agents, flavourants, essential oils, moisturizers, preservatives, and any other cosmetically safe components that may be useful.

In one embodiment, the formulation is the form of a balm (e.g., lipbalm, lipstick, lip gloss) comprising:

(a) polyethylene glycol, as described herein;
(b) none or one or more base forming components;
(c) none or one or more sunscreen components;
(d) none or one or more colouring agents;
(e) none or one or more flavourants;
(e) none or one or more essential oils;
(f) none or one or more moisturizers; and
(f) none or one or more preservatives.

Emulsion Formulations

In one embodiment, the formulation is a composition in the form of an emulsion.

Such formulations may be lipophilic in nature (i.e., fat-based) or hydrophilic in nature (i.e., water-based) and can take on various specific forms (e.g., emulsion-based creams, lotions, and the like). The emulsions used in preparing the lipophilic and hydrophilic formulations include oil-in-water (O/W) emulsions, water-in-oil (W/O) emulsions, water-in-oil-in-water (W/O/W) emulsions, oil-in-water-in-oil (O/W/O) emulsions, lipodispersions, and hydrodispersions. Emulsions may contain, for example, fats, oils, waxes, or other fat bodies, as well as water and one or more emulsifiers, as are typically used for such a type of formulation.

The oil phase of an emulsion may be, for example, chosen from: mineral oils and mineral waxes; oils, such as triglycerides of capric acid, caprylic acid, or castor oil; fats, waxes, and other natural and synthetic fatty bodies, preferably esters of fatty acids with alcohols of low carbon number, e.g., with isopropanol, propylene glycol or glycerol, or esters of fatty alcohols with alkanoic acids of low carbon number or with fatty acids; alkyl benzoate; silicone oils, such as dimethylpolysiloxanes, diethylpolysiloxanes, diphenylpolysiloxanes, and mixed forms thereof. The oil phase of an emulsion may be, for example, chosen from: esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms; esters of aromatic carboxylic acids and saturated and/or unsaturated, branched and/or unbranched alcohols with a chain length of from 3 to 30 carbon atoms. Such ester oils may, for example, be chosen from isopropyl myristate, isopropyl palmitate, isopropyl stearate, isopropyl oleate, n-butyl stearate, n-hexyllaurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g., jojoba oil. In addition, the oil phase may be, for example, chosen from: branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids with a chain length of from 8 to 24, in particular 12-18, carbon atoms. The fatty acid triglycerides may, for example, be chosen from: the group of synthetic, semisynthetic and natural oils, e.g., olive oil, sunflower oil, soybean oil, peanut oil, rapeseed oil, almond oil, palm oil, coconut oil, palm kernel oil, and the like.

Any mixtures of such oil and wax components may also be used. It may also, for example, be advantageous to use waxes, for example cetyl palmitate, as the sole lipid component of the oil phase. The oil phase may also have a content of cyclic or linear silicone oils or consist entirely of such oils, although it is preferred to include an oil phase component in addition to the silicone oil or oils.

The aqueous phase may, for example, comprise alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g., ethanol, isopropanol, 1,2-propanediol, glycerol. In addition, the aqueous phase may further comprise one or more thickeners, for example, selected from: silicon dioxide, aluminum silicates, polysaccharides and derivatives thereof, e.g., hyaluronic acid, xanthan gum, hydroxypropylmethylcellulose, preferably selected from the group of polyacrylates, preferably a polyacrylate from the group of so-called carbopols.

The emulsion formulations comprise PEG, as described herein. In one embodiment, the emulsion formulation comprises PEG, as described herein, in concentrations of about 0.1% to about 100% by weight based on the overall weight of the emulsion formulation. In other embodiments, the range is about 50% to about 100% by weight, or about 60% to about 100% by weight, or about 70% to about 100% by weight, or about 80% to about 100% by weight, or about 90% to about 100% by weight, based on the overall weight of the emulsion formulation.

The creams, lotions, etc. prepared using the emulsions, hydrodispersions, or lipodispersions can include a variety of further components. For example, the compositions may further comprise one or more sunscreen components, as described herein, and/or one or more antioxidants, as described herein, as well as preservatives, solubilizers, fragrances, conditioning agents, and/or moisturizers.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

EXAMPLES

The study described herein was part of a single centre Phase I/II, placebo controlled, randomized, double-blind study, to treat recurrent herpes labialis by topical treatment with an ointment.

Study Goal

The primary objective was to determine the number of herpes labialis relapses during six months of prophylactic and acute treatment.

Evaluation

A relapse was defined as recurring herpes labialis signs and symptoms such as erythema, papule, vesicle, ulceration, erosion, swelling, etc.

The maximal lesion area was evaluated by measuring the length and the width of the lesion. The outcome of the multiplication of these data is the area ($mm^2$).

The duration of herpes labialis relapse episode was evaluated by counting the days from the first prodromal signs of cold sore (feeling of tension, hypersensitivity of the skin, tingling, burning, and itching) to complete healing. Healing was defined as the loss of crust (residual erythema may be present) and/or the cessation of all symptoms. The last remaining effect (either normal skin or cessation of all symptoms) was recorded and used as the endpoint of lesion duration.

The degree of pain/discomfort during herpes relapse episode was evaluated by a 100 mm visual analogue scale (VAS). Patients marked daily on the VAS their level of pain experienced during the day. Patients recorded their pain level during the whole relapse treatment (14 days).

Subject Selection

A total of 20 patients were recruited. Male and female adult patients with a history of recurrent herpes labialis (at least eight recurrences in the previous year, with no limitations on the maximum number of recurrences) were recruited for the study.

Patients were enrolled in the study if they fulfilled the following inclusion criteria:

(1) 18 to 50 years of age;
(2) Medical history of herpes labialis with lesions on the lips or in the perioral area (<1 cm from the border of the lips);
(3) At least eight recurrences of herpes labialis during the previous year before being enrolled in the study;
(4) Ability and willingness to participate in the study; and
(5) Voluntarily provided written informed consent.

Patients who fulfilled any one of the following criteria were excluded from the study:

(1) Females with child bearing potential who are not using a reliable, medically accepted method of birth control (e.g., surgical, intra-uterine contraceptive device, birth control pill, double barrier, hormone delivery systems such as implants or injectibles, condoms or diaphragm (each in combination with contraceptive creams, foams, etc.);
(2) Pregnant or breast feeding female, or women planning a pregnancy during the trial;
(3) Medical history of immunosuppression by radiotherapy, chemo therapy, immunomodulatory drugs, or HIV;
(4) Participation in another clinical study within 30 days prior to beginning of this study;
(5) Medical history of any severe diseases like hepatitis, renal or liver dysfunction, cardiovascular, gastrointestinal, malignant tumor(s), or psychiatric disorders etc., which might influence the assessments or conduct of the trial;
(6) Intake or application of antivirals or other prohibited concomitant medication within 30 days prior to the beginning of this study, or intention to take such drugs during the trial;
(7) Use of anti-inflammatory medications and steroids during the course of the study;
(8) Eczema herpeticatum or any history of other skin disease that would predispose to eczema herpeticatum;
(9) Any abnormal perioral skin condition;
(10) Known or suspected allergic or adverse response to PEG;
(11) Inability to follow the study protocol;
(12) Medical history of alcohol and/or drug abuse within the previous 12 months before enrollment in the study.

Study Design

Patients were not informed of the chemical content of the ointment used in the study; specifically, they were not informed that it was, or contained, PEG, or any other ingredient.

The first application of PEG ointment was performed at the study site on the second visit. After the first application, the patient was observed for 30 minutes to ensure his/her safety and well-being. If the patient has an acute relapse of recurrent Herpes labialis at Visit 2, PEG ointment was then administered five times a day for 14 days (acute dosing) over the whole lips. Each time about 1.5 cm of ointment was applied on the upper lip and 1.5 cm on the lower lip (both together ca. 0.2 g). After these 14 days, the PEG ointment was applied twice daily, for 6 months (the 14 days of acute treatment are included in these 6 months) over the whole lips (prophylaxis dosing). In case of no current relapse at Visit 2 (no visible signs or symptoms like feeling of tension, hypersensitivity of the skin, tingling, burning, and itching of Herpes labialis), PEG ointment was applied twice daily, for 6 months, over the whole lips.

Each patient applied all further applications at home by him-/herself. Within 48 hours after the first application, the investigator contacted the patient by telephone to find out about the experience of administration, comfort, discomfort, adverse reaction and the general well-being. To check the compliance and any herpes symptoms during the whole study, the patient was asked to record all applications and any symptoms (feeling of tension, hypersensitivity of the skin, tingling, burning, and itching) into a diary (making a cross for conducted applications). In addition, the patient was asked to fill in a visual analogue scale (VAS) to record pain levels at the end of each day of the acute herpes relapse episode.

All relapses were treated as soon as the first symptoms (prodromal symptoms such as: feeling of tension, hypersensitivity of the skin, tingling, burning, and itching) occur for 14 days with PEG ointment 5 times a day.

During an acute phase (relapse), patients were asked to come to the study site for visits on day 1 (within 24 hours after first symptoms), day 5, day 10 and day 14. On day 15, the prophylaxis period started again with two applications daily until the next relapse or then end of the study (6 months). During the prophylaxis period, the patients were required to visit the study site every 60 days for control examination and to receive study medication.

Screening Visit (Visit 1). Interested patients were invited to the study site, to discuss the study in detail in a medical education interview and to receive the patient information sheet, which contained all study details. Upon signing the informed consent form at the study site, the investigator asked the patient for the number of herpes relapses they had suffered in the previous year. Eligible patients were enrolled in the study and received consecutive patient numbers.

Medical Examination and First Application (Visit 2). Enrolled patients had a physical examination and the investigator collected and recorded the following data and performed the following examinations: (1) medical history, especially regarding to recurrent herpes labialis but also including allergies, especially against PEG; (2) complete physical examination including skin (especially perioral region), ear, nose, throat, neck and thyroid, cardiopulmonary system, lymph nodes, nervous system, and muscular skeletal system, and including vital signs (blood pressure, heart rate); (3) for women of child bearing potential, a urine pregnancy test was performed; a negative result was required in order to progress in the study.

The first dose of the PEG ointment was administered by the patient at the study site (under the supervision of the investigator), where patients were observed for at least 30 minutes to ensure their safety and well-being. When no adverse reactions occurred, patients were released and asked to apply all further dosages at home accordingly, until eventual relapses occurred. In this case, patients were asked to return to the study site within 24 hours, as soon as they feel any prodromal signs such as feeling of tension, hypersensitivity of the skin, tingling, burning, and itching.

Patients were given a patient's diary and were instructed how to fill in the diary during the whole study period. The patients diary was to contain a record of all applications of the PEG ointment, as well as any symptoms with regard to Herpes labialis (e.g., visible signs like erythema, vesicle, papule, etc., and also feelings like tingling, burning, itching, etc.), and any other changes in well-being (adverse events).

The patients were required to tick the respective boxes in the diary and to make notes about pain/discomfort at the lips, and adverse events, as applicable. During a Herpes labialis relapse period, the patients were asked to mark the level of pain/discomfort on a 100 mm visual analogue scale (VAS) on each day in their diary.

Phone call (within 48 hours after first application). Within 48 hours after the first application of PEG ointment, the investigator contacted the patient by telephone to find out about the experience of drug administration, comfort, discomfort, adverse event and the general well-being.

Two-Month Contact or Control Visits (Visits 3, 4 and 5). At each contact/control visit, which were performed 60±5 days (Visit 3), 120±5 days (Visit 4), 180±5 days (Visit 5) after Visit 2, the investigator examined the lips of the patient for any kind of abnormalities and asked the patient for his/her experience with ointment application and compliance, and about the occurrence of any adverse events since the last visit.

Patients also brought along their diary which was checked by the investigator for compliance and any other entries. If the patient could not come to the study site, because of indisposition, the visit was replaced exceptionally by telephone call.

In case of an acute relapse on a scheduled visit, the procedure was the same as described in for Visit 1a.

Visit 5 was the final examination visit (end of the study). In addition to the examinations described for the control visits, the final examination also included a complete physical examination including skin (especially perioral region), ear, nose, throat, neck and thyroid, cardiopulmonary system, lymph nodes, nervous system, and muscular skeletal system, and including vital signs (blood pressure, heart rate).

Additional Visits.

In case of Herpes labialis relapse, patients were asked to come to the study site as soon as they recognized any prodromal signs and symptoms on their lips. During the acute phase of relapse, the patients came to the study site on Days 1, 5, 10 and 14 (±24 hours) after start of the first signs and symptoms, and were asked to continue with their record in their diary.

Visit 1a, (Day 1 of Acute Phase, within 24 Hours).

As soon as patients recognised first symptoms of Herpes labialis (feeling of tension, hypersensitivity of the skin, tingling, burning, and itching), they were required to call the investigator to arrange a visit at the study site within 24 hours. During this visit, an examination was conducted by the investigator, which included: recording the location of the lesion, measurement of the lesion, judgement of the state of lesion (erythema, papule, vesicle, ulcerated, eroded, hard crusted, dry flaking, residual swelling, healed and associated with pain). Patients were also required to bring along their diary to give to the investigator who evaluated the data and checked for compliance. The investigator also asked the patient's experience about taking PEG ointment and about any problems that might have occurred.

In case of another relapse, patients were required to come to the study site within 24 hours of first symptoms of recurrent Herpes labialis (feeling of tension, hypersensitivity of the skin, tingling, burning, and itching), as above. Should any side effects occur, the patient was required to comet to the study site as soon as possible for an examination.

Visit 2a, (Day 5 of Acute Phase, ±1 Day).

The same procedure was followed as described for Visit 1a.

Visit 3a, (Day 10 of Acute Phase, ±1 Day).

The same procedure was followed as described for Visit 1a.

Visit 4a, (Day 14 of Acute Phase, ±1 Day).

This was the last visit during the acute phase. The investigator confirmed that the lesion has decayed and thus the relapse was over. Should the relapse be over earlier than 14 days, PEG ointment was still administered five times a day until 14 days were over. The reason for this was potential ongoing subclinical viral replication. Therefore, patients were told to continue application of the PEG ointment until 14 days were over. Even if the relapse was not over within 14 days, PEG ointment treatment changed to twice daily until the next relapse or end of the study.

PEG Ointment

The PEG ointment used in the study was 85 wt % PEG 400 (INCI name PEG-8) and 15 wt % PEG 8000 (INCI name PEG-180), and was produced according to good manufacturing practice (GMP) Guidelines.

The quality of the PEG conformed with the standards set in the European Pharmacopeia monographs for Macrogol 400 and Macrogol 8000, respectively (see, e.g., "Macrogols" Monograph, European Pharmacopoeia 5.0, January 2005:1444, pp. 1950-1951). Typical specifications for Macrogol 400 and Macrogol 8000 are summarised in the following table.

TABLE 3

| Property | PEG 400 (Macrogol 400) | PEG 8000 (Macrogol 8000) |
|---|---|---|
| Appearance | Clear, viscous colourless or almost colourless hygroscopic liquid | White or almost white solid with a waxy or paraffin-like appearance |
| Solubility | Miscible with water, very soluble in acetone, in alcohol, and in methylene chloride, practically insoluble in fatty oils and in mineral oils | Very soluble in water and in methylene chloride, practically insoluble in alcohol and in fatty oils and in mineral oils |
| Kinematic viscosity at 98.9° C. (mm$^2$/s) | 94-116 | 240-472 |
| Dynamic viscosity at 20° C. (mPa * s) | 105-130 | 260-510* |
| Density (g/mL) | 1.120 | 1.080* |
| Hydroxyl value | 264-300 | 12-16 |
| Heavy metals as Pb (ppm) | ≤20 | ≤20 |

TABLE 3-continued

| Property | PEG 400 (Macrogol 400) | PEG 8000 (Macrogol 8000) |
|---|---|---|
| Water (% by mass) | ≤2 | ≤1 |
| Formaldehyde (ppm) | ≤30 | ≤30 |
| Sulphated ash (% by mass) | ≤0.2 | ≤0.2 |
| Ethylene oxide (ppm) | ≤1 | ≤1 |
| Dioxan (ppm) | ≤10 | ≤10 |
| Ethylene glycol and diethylene glycol (% by mass) | ≤0.4 | ≤0.4 |
| Acidity or alkalinity (mL 0.1N NaOH) | ≤0.1 | ≤0.1 |

*50% mass/mass solution.

The weight average molecular weight of the PEG 400 was not less than 95.0% and not more than 105.0% of the nominal value of 400.

The weight average molecular weight of the PEG 8000 was not less than 87.5% and not more than 112.5% of the nominal value of 8000.

The patients were not told what the ointment in the study contained.

Topical Administration

The patients were treated with PEG ointment, which was applied directly onto the whole lips (1.5 cm of ointment on the upper lip and 1.5 cm on the lower lip) so that they are completely covered with ointment. It was important that damage, lesions or other abnormalities (not associated Herpes labialis) were not present on the lips or on the skin (<1 cm from border of the lips).

The first application was administered by the patient at the study site, under the supervision of the investigator. In the prophylaxis period, the drug was applied twice daily by the patient at their home. In the acute phase, the drug was applied five times daily by the patient at their home.

Concomitant Medication

The following medications were prohibited during the study and within 30 days prior to the beginning of the study: immunomodulatory drugs; cytostatics; any kind of antivirals; Compeed™ Cold Sore Patch; anti-inflammatory medications; steroids; lip cosmetics (e.g., lipstick, lip-sunscreen, lip-balsam, etc.). All other medications necessary for the well-being of the subject were permitted, but were accurately recorded in the case report form by the investigator.

Assessment

Determination of the Number of Relapses.

For each individual patient, any herpes relapse occurring during 6 months of prophylactic treatment PEG was documented.

Determination of the Maximal Lesion Area.

The lesion area was defined as the product of the length and the width. For measuring this, a calliper rule or a small scale was used. The results were noted in mm$^2$ along with the observed stage. The maximal lesion area was determined at every additional visit during a Herpes relapse episode.

Determination of the Duration.

For determining the duration of an episode, the days from the first prodromal signs of cold sore (feeling of tension, hypersensitivity of the skin, tingling, burning, and itching) until complete healing were counted. Healing was defined as the loss of crust (residual erythema may be present) and/or the cessation of all symptoms. The last remaining effect (either normal skin or cessation of all symptoms) was recorded and used as the endpoint of lesion duration.

Determination of the Degree of Pain/Discomfort.

For determining the degree of pain during a relapse, a 100 mm visual analogue scale (VAS) was used (where 0 indicated no pain and 10 indicated unbearable pain). During the whole relapse time (14 days) patients marked on the VAS at the end of every day, the level of pain that they have experienced within the past 24 hours (only regarding their cold sore). The VAS was distributed with the diary to each patient; at each of the 'additional visits' they brought the completed diaries to the study site, where they were evaluated by the investigator.

For a more precise description of the symptoms (and determination of severity), patients were also required to note their feelings (prodromal signs) as illustrated in the following table.

TABLE 4

Patient Rating of Symptoms

| Tension | Hypersensitivity | Tingling | Burning | Itching | Score |
|---|---|---|---|---|---|
| None | None | None | None | None | 0 |
| Slight sensation | Slight sensation | Slight sensation | Slight sensation | Slight sensation | 1 |
| Definite sensation | Definite sensation | Definite sensation | Definite sensation | Definite sensation | 2 |
| Severe Sensation | Severe Sensation | Severe Sensation | Severe Sensation | Severe Sensation | 3 |

Adverse Events

The well-being of the patients was ascertained by neutral questioning ("How are you?"). The investigator was responsible for reporting all adverse events occurring during the course of the study. The intensity of adverse events was assessed as being mild (hardly noticeable, negligible impairment of well-being), moderate (marked discomfort, but tolerable without immediate relief) or severe (overwhelming discomfort, calling for immediate relief).

An adverse event (AE) was defined as any untoward medical occurrence in a patient or clinical investigation subject administered the PEG ointment and which does not necessarily have a causal relationship with this treatment. An adverse event could therefore be any unfavourable and unintended sign (including an abnormal laboratory finding), symptom, or disease temporally associated with the use of the PEG ointment, whether or not related to the PEG ointment.

A serious adverse event (SAE) was defined as any untoward medical occurrence that at any dose: resulted in death; was life-threatening; required hospitalization or prolongation of current hospitalization; resulted in persistent or significant disability/incapacity; was a congenital anomaly/birth defect (this refers to a congenital anomaly in an offspring of a subject or subject who received PEG ointment); was any important medical event and any event which, though not included in the above, might jeopardise the subject or might require intervention to prevent one of the outcomes listed above.

Any other medically important condition that might not be immediately life-threatening or result in death or hospitalization but might jeopardize the subject or might require intervention to prevent one of the outcomes listed above would also (i.e., based on medical and scientific judgment) usually be considered to be serious. These include, for example: intensive treatment at home for allergic bronchospasm; certain laboratory abnormalities (e.g., blood dyscrasias); convulsions that do not result in hospitalisation; development of drug dependency or drug abuse.

Pregnancy per se did not classify as an adverse event. However, adverse events related to a pregnancy were reported like any other adverse events. Pregnancy was confirmed by a reliable laboratory test. Pregnant subjects were to be immediately withdrawn from the clinical study.

Premature Study Termination

Premature study treatment termination for any reason was fully documented. Every reasonable effort was made to maintain subject protocol compliance and participation in the study. The investigator monitored patient protocol compliance at each control visit, by looking at the diary in which the patient has to tick boxes for the conducted applications of the study drug. Patients were free to withdraw from the study at any time, without giving a reason and without prejudicing further treatment. The investigator was permitted to withdraw patients from the study for safety reasons. Patients were necessarily withdrawn from further study participation if: pregnancy occurred; relevant safety issues occurred; or patients were non-compliant to the study protocol.

Results

As described above, 20 patients were recruited for the study. Four of the patients were withdrawn during the study, leaving 16 patients to complete the study.

The 4 patients were withdrawn from the study for the following reasons: (1) patient did not return, and was lost to follow-up; (2) patient found the study to be too time consuming; patient was not so mobile any more due to a broken leg; (3) patient found the study caused too many constraints on day-to-day life; treatment caused dry lips and patient sensed little efficacy; and (4) patient discontinued study due to an undesired event (lichen and itch).

Data regarding the number of relapses per year of herpes labialis, both before the study and during the study are summarized in the following table.

TABLE 5

Relapses Before and During Study

| Patient No. | Number of relapses per year before study | Number of relapses during six-month study |
|---|---|---|
| 1 | 20 | 0 |
| 14 | 15 | 0 |
| 13 | 14 | 0 |
| 2 | 11 | 0 |
| 7 | 10 | 0 |
| 3 | 9 | 0 |
| 4 | 8 | 0 |
| 12 | 8 | 0 |
| 10 | 15 | 1 |
| 15 | 15 | 1 |
| 11 | 10 | 1 |
| 16 | 9 | 1 |
| 9 | 12 | 2 |
| 8 | 20 | 3 |
| 6 | 14 | 3 |
| 5 | 10 | 4 |

Of the 16 patients completing the study, 8 (50%) reported no relapses during the six-month study period.

Of the 16 patients completing the study, 12 (75%) reported 0 or 1 relapses during the six-month study period.

Of the 16 patients completing the study, 13 (81%) reported from 0 to 2 relapses during the six-month study period.

Of the 16 patients completing the study, all (100%) reported from 0 to 4 relapses during the six-month study period.

Again, all patients were recruited on the basis of at least eight recurrences in the previous year, with no limitations on the maximum number of recurrences.

In 13 patients (81%), treatment during the six-month study period resulted in at least a two-fold reduction in the number of relapses per year.

In 12 patients (75%), treatment during the six-month study period resulted in at least a four-fold reduction in the number of relapses per year.

In 8 patients (50%), treatment during the six-month study period resulted in a greater than four-fold reduction in the number of relapses per year (in one patient, reaching a greater than ten-fold reduction in the number of relapses per year).

The results are also illustrated graphically in FIG. 1, which is a bar graph illustrating the reduction in the number of outbreaks (relapses) of herpes labialis in the patients of the study described herein. Both the % of patients and the cumulative % of patients are reported for each of 100%, 90+%, 80%+, 70%+, and 60%+reduction in the number of outbreaks (relapses).

It is clear from the data that treatment with the PEG ointment very greatly reduced the number of relapses of herpes labialis per year.

Patient rating of user-friendliness during the prophylactic phase (on a scale from 1 to 10, where the higher the value, the greater the satisfaction, as summarised in the following table) was favourable. 62% (10/16) of patients rated user-friendliness at 8 or greater. 81% (13/16) of patients rated user-friendliness at 5 or greater.

TABLE 6

User-friendliness During the Prophylactic Phase

| Patient No. | 1 | 2 | 3 | 4 | 5 | 6 | 7 | 8 | 9 | 10 |
|---|---|---|---|---|---|---|---|---|---|---|
| 1 | | | | X | | | | | | |
| 2 | | | | | | | | | | X |
| 3 | | | | | | | | X | | |
| 4 | | | | | | | | X | | |
| 5 | | | | | X | | | | | |
| 6 | | | | | | | | | | X |
| 7 | | | | | | | | | X | |
| 8 | | | | | | | | X | | |

TABLE 6-continued

User-friendliness During the Prophylactic Phase

| Patient No. | 1 | 2 | 3 | 4 | 5 | 6 | 7 | 8 | 9 | 10 |
|---|---|---|---|---|---|---|---|---|---|---|
| 9 | | | | | | | | X | | |
| 10 | | | | | | | | X | | |
| 11 | | | | X | | | | | | |
| 12 | | | | | | | | | | X |
| 13 | | | | | | | | X | | |
| 14 | | | | | | | X | | | |
| 15 | | | | | | X | | | | |
| 16 | | X | | | | | | | | |
| Total | 0 | 2 | 0 | 1 | 1 | 1 | 1 | 5 | 2 | 3 |

Patient rating of user-friendliness during the acute phase (on a scale from 1 to 10, where the higher the value, the greater the satisfaction, as summarised in the following table) was favourable. 88% (7/8) of patients who answered rated user-friendliness at 5 or greater.

TABLE 7

User-friendliness During the Acute Phase

| Patient No. | 1 | 2 | 3 | 4 | 5 | 6 | 7 | 8 | 9 | 10 |
|---|---|---|---|---|---|---|---|---|---|---|
| 1 | | | | | | | | | | |
| 2 | | | | | | | | | | |
| 3 | | | | | | | | | | |
| 4 | | | | | | | | | | |
| 5 | X | | | | | | | | | |
| 6 | | | | | | | | | | X |
| 7 | | | | | | | | | | |
| 8 | | | | | | | X | | | |
| 9 | | | | | | | | | X | |
| 10 | | | | | | | X | | | |
| 11 | | | | | | | | | | X |
| 12 | | | | | | | | | | |
| 13 | | | | | | | | | | |
| 14 | | | | | | | | | | |
| 15 | | | | | | | | | | X |
| 16 | | | | | X | | | | | |
| Total | 1 | 0 | 0 | 0 | 1 | 0 | 2 | 0 | 1 | 3 |

Patient satisfaction with the medicament (on a scale from 1 to 10, where the higher the value, the greater the satisfaction, as summarised in the following table) was very favourable. 50% (8/16) of the patients rated satisfaction at the maximum 10. 94% (15/16) of the patients rated satisfaction at 5 or greater.

TABLE 8

Satisfaction with the Medicament

| Patient No. | 1 | 2 | 3 | 4 | 5 | 6 | 7 | 8 | 9 | 10 |
|---|---|---|---|---|---|---|---|---|---|---|
| 1 | | | | | | | | | | X |
| 2 | | | | | | | | | | X |
| 3 | | | | | | | | | | X |
| 4 | | | | | | | | | | X |
| 5 | X | | | | | | | | | |
| 6 | | | | | X | | | | | |
| 7 | | | | | | | | | | X |
| 8 | | | | | | | | X | | |
| 9 | | | | | | | X | | | |
| 10 | | | | | | X | | | | |
| 11 | | | | | | | X | | | |
| 12 | | | | | | | | | X | |
| 13 | | | | | | | | | | X |
| 14 | | | | | | | | | | X |
| 15 | | | | | | | | | | X |
| 16 | | | | | | | | X | | |
| Total | 1 | 0 | 0 | 0 | 1 | 0 | 2 | 3 | 1 | 8 |

In addition, overall patient satisfaction with the treatment (on a scale from 1 to 10, where the higher the value, the greater the satisfaction, as summarised in the following table) was very favourable. 81% (13/16) of the patients rated satisfaction at 5 or greater.

TABLE 9

Overall Satisfaction with the Treatment

| Patient No. | 1 | 2 | 3 | 4 | 5 | 6 | 7 | 8 | 9 | 10 |
|---|---|---|---|---|---|---|---|---|---|---|
| 1 | | | | | X | | | | | |
| 2 | | | | | | | | | | X |
| 3 | | | | | | | | | X | |
| 4 | | | | | | | | | X | |
| 5 | X | | | | | | | | | |
| 6 | | X | | | | | | | | |
| 7 | | | | | | | | X | | |
| 8 | | | | | | | | X | | |
| 9 | | | | | | | | | X | |
| 10 | | | | | | | | X | | |
| 11 | | | | | X | | | | | |
| 12 | | | | | | | | | | X |
| 13 | | | | | | | | | X | |
| 14 | | | X | | | | | | | |
| 15 | | | | | X | | | | | |
| 16 | | | | | | | | X | | |
| Total | 1 | 1 | 0 | 1 | 3 | 0 | 0 | 4 | 4 | 2 |

Additional data, not shown here, demonstrate that the positive effects of PEG are not substantially diminished when the formulation is diluted with up to 20% by weight of a non-PEG component. Specifically, in a parallel study, where the PEG ointment was replaced with an ointment consisting of 80% by weight PEG (as a mixture of 85 wt % PEG 400 and 15 wt % PEG 8000) and 20% by weight of another non-PEG component, the rate of relapse of herpes labialis was substantially reduced, but not quite to the extent reported herein for undiluted PEG.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these publications are provided below. Each of these publications is incorporated herein by reference in its entirety into the present disclosure, to the same extent as if each individual publication was specifically and individually indicated to be incorporated by reference.

Buenzli, D., et al., 2004, "Seroepidemiology of herpes simplex virus type 1 and 2 in western and southern Switzerland in adults aged 25-74 in 1992-93: a population-based study", *BMC Infect. Dis*, Vol. 4, No. 10.

Lukas, B., et al., 1988, "Antiherpetically active lipstick and the use thereof for the treatment of disorders of the lips and other areas of the face caused by human herpes viruses", U.S. Pat. No. 4,762,715 granted 9 Aug. 1988.

Vitins, P., et al., 2008, "Cyclodextrin Formulations", international patent publication number WO 2008/087034 A2 published 24 Jul. 2008.

Whitley, R. J., 1990, "Herpes simplex viruses", in *Virology*, (Fields, B. N., et al., eds., Raven Press, New York, USA), pp. 1852-1854.

Young, T. B., et al., 1988, "Cross-sectional study of recurrent herpes labialis", *Am. J. Epidemiol.*, Vol. 127, pp. 612-625.

The invention claimed is:

1. A method of reducing the rate of relapse of herpes labialis in a patient, comprising topically administering a therapeutically effective amount of a composition comprising polyethylene glycol;
    wherein the method is performed for a duration of at least 4 weeks;
    wherein the topical administration is from once daily to five times daily;
    wherein the topical administration is on and/or around the lips of said patient;
    wherein the composition contains about 90 to 100% polyethylene glycol by weight of the overall composition;
    wherein the polyethylene glycol is polyethylene glycol polymer having weight average molecular weight (Mw) of about 300 to about 500, and wherein the polyethylene glycol is used as the sole anti-herpetic agent in the composition.

2. A method according to claim 1, wherein the method is performed for a duration of at least 8 weeks.

3. A method according to claim 1, wherein the method is performed for a duration of at least 3 months.

4. A method according to claim 1, wherein the method is performed for a duration of at least 6 months.

5. A method according to claim 1, wherein the method is performed for a duration of at least 1 year.

6. A method according to claim 1, wherein the topical administration is from once daily to three times daily.

7. A method according to claim 1, wherein the topical administration is on at least a part of the lips and the surrounding facial skin <1 cm from the border of the lips of said patient.

8. A method according to claim 1, wherein the therapeutically effective amount is from about 0.02 g to about 2 g per administration.

9. A method according to claim 1, wherein the polyethylene glycol is polyethylene glycol polymer having weight average molecular weight (Mw) of about 400.

10. A method according to claim 9, wherein the method is performed for a duration of at least 8 weeks.

11. A method according to claim 9, wherein the method is performed for a duration of at least 3 months.

12. A method according to claim 9, wherein the method is performed for a duration of at least 6 months.

13. A method according to claim 9, wherein the method is performed for a duration of at least 1 year.

14. A method according to claim 9, wherein the topical administration is from once daily to three times daily.

15. A method according to claim 9, wherein the topical administration is on at least a part of the lips and the surrounding facial skin <1 cm from the border of the lips of said patient.

16. A method according to claim 9, wherein the therapeutically effective amount is from about 0.02 g to about 2 g per administration.

17. A method of reducing the rate of relapse of herpes labialis in a patient, comprising topically administering a therapeutically effective amount of a composition comprising polyethylene glycol;
    wherein the method is performed for a duration of at least 4 weeks;
    wherein the topical administration is from once daily to five times daily;
    wherein the topical administration is on and/or around the lips of said patient;
    wherein the composition contains about 85 to 100% polyethylene glycol by weight of the overall composition;
    wherein the polyethylene glycol is a mixture of two polyethylene glycol polymers:
    (a) polyethylene glycol polymer with a weight average molecular weight (Mw) of about 300 to about 500; and
    (b) polyethylene glycol polymer with a weight average molecular weight (Mw) of about 6,000 to about 10,000;
    wherein the weight ratio of component (a) to component (b) is about 5:1 to about 10:1, and wherein the polyethylene glycol is used as the sole anti-herpetic agent in the composition.

18. A method according to claim 17, wherein the method is performed for a duration of at least 8 weeks.

19. A method according to claim 17, wherein the method is performed for a duration of at least 3 months.

20. A method according to claim 17, wherein the method is performed for a duration of at least 6 months.

21. A method according to claim 17, wherein the method is performed for a duration of at least 1 year.

22. A method according to claim 17, wherein the topical administration is from once daily to three times daily.

23. A method according to claim 17, wherein the topical administration is on at least a part of the lips and the surrounding facial skin <1 cm from the border of the lips of said patient.

24. A method according to claim 17, wherein the therapeutically effective amount is from about 0.02 g to about 2 g per administration.

25. A method according to claim 17, wherein:
    the polyethylene glycol is a mixture of two polyethylene glycol polymers:
    (a) polyethylene glycol polymer with a weight average molecular weight (Mw) of about 400; and
    (b) polyethylene glycol polymer with a weight average molecular weight (Mw) of about 8,000;
    wherein the weight ratio of component (a) to component (b) is about 5:1 to about 8:1.

26. A method according to claim 25, wherein the method is performed for a duration of at least 8 weeks.

27. A method according to claim 25, wherein the method is performed for a duration of at least 3 months.

28. A method according to claim 25, wherein the method is performed for a duration of at least 6 months.

29. A method according to claim 25, wherein the method is performed for a duration of at least 1 year.

30. A method according to claim 25, wherein the topical administration is from once daily to three times daily.

31. A method according to claim 25, wherein the topical administration is on at least a part of the lips and the surrounding facial skin <1 cm from the border of the lips of said patient.

32. A method according to claim 25, wherein the therapeutically effective amount is from about 0.02 g to about 2 g per administration.

33. The method of claim 1, wherein the administering is initiated when the patient has no symptoms of herpes labialis infection.

34. The method of claim 17, wherein the administering is initiated when the patient has no symptoms of herpes labialis infection.

35. The method of claim 1, wherein the composition does not contain a therapeutically effective amount of an additional antiherpetic agent.

36. The method of claim 17, wherein the composition does not contain a therapeutically effective amount of an additional antiherpetic agent.

37. The method of claim 1, wherein the composition consists of:
  (i) polyethylene glycol, which is used as the sole anti-herpetic agent or
  (ii) polyethylene glycol, one or more pharmaceutically inert excipients and, optionally, a non-therapeutically effective amount of one or more additional antiherpetic agents;
and wherein the administering is initiated when the patient has no symptoms of herpes labialis.

38. The method of claim 17, wherein the composition consists of:
  (i) polyethylene glycol, which is used as the sole anti-herpetic agent or
  (ii) polyethylene glycol, one or more pharmaceutically inert excipients and, optionally, a non-therapeutically effective amount of one or more additional antiherpetic agents;
and wherein the administering is initiated when the patient has no symptoms of herpes labialis.

* * * * *